US006424860B1

(12) United States Patent
Karlsson et al.

(10) Patent No.: US 6,424,860 B1
(45) Date of Patent: Jul. 23, 2002

(54) MYOCARDIAL ISCHEMIA AND INFARCTION ANALYSIS AND MONITORING METHOD AND APPARATUS

(75) Inventors: Per Karlsson, Taby; Gunilla Lundahl, Lidingo; Michael Oljemark, Saltsjo-Boo; Johan Ubby, Vaxholm; Bengt Arne Sïoovist, Vastra Frolunda, all of (SE)

(73) Assignee: Ortivus AB, Taby (SE)

( * ) Notice: Subject to any disclaimer, the term of this patent is extended or adjusted under 35 U.S.C. 154(b) by 0 days.

(21) Appl. No.: 09/436,908

(22) Filed: Nov. 9, 1999

Related U.S. Application Data

(63) Continuation-in-part of application No. 09/040,876, filed on Mar. 18, 1998, now Pat. No. 6,038,469, which is a continuation-in-part of application No. 08/653,448, filed on May 24, 1996, now Pat. No. 5,819,741, which is a continuation-in-part of application No. 08/320,511, filed on Oct. 7, 1994, now Pat. No. 5,520,191.

(51) Int. Cl.$^7$ ............................................. A61B 4/0452

(52) U.S. Cl. ..................................................... 600/512

(58) Field of Search ................................ 600/509, 515, 600/518, 516, 517, 512

(56) References Cited

U.S. PATENT DOCUMENTS

| 3,548,813 A | 12/1970 | Berner |
| 3,858,034 A | 12/1974 | Anderson |
| 4,213,465 A | 7/1980 | Ranheim |
| 4,216,526 A | 8/1980 | Karwowski |
| 4,570,225 A | 2/1986 | Lundy |
| 4,850,370 A | 7/1989 | Dower |
| 4,924,875 A | 5/1990 | Chamour |
| 5,038,800 A | 8/1991 | Oha |
| 5,083,571 A | 1/1992 | Prichep |
| 5,375,604 A | 12/1994 | Kelly et al. |
| 5,410,473 A | 4/1995 | Kaneko et al. |
| 5,441,047 A | 8/1995 | David et al. |
| 5,469,857 A | 11/1995 | Laurent et al. |
| 5,520,191 A | 5/1996 | Karlsson et al. |
| 5,544,661 A | 8/1996 | Davis et al. |

FOREIGN PATENT DOCUMENTS

| EP | 0711531 | 5/1996 |
| WO | WO9802090 | 1/1998 |

OTHER PUBLICATIONS

High Resolution ECG System For Micropotential Analysis & Shape Classification, Rix et al., Annual International Conference of the IEEE Engineering in Medicine and Biology Society, vol. 13, No. 2 (1991).

Mikael Dellborg, Dynamic Vectorcardiographic Monitoring of Patients During Myocardial Ischemia and Infarction, (Dept. of Med. Univ. of Goteborg, Ostro Hospital, Goteborg, Sweden, 1991).

(List continued on next page.)

Primary Examiner—Scott M. Getzow
(74) Attorney, Agent, or Firm—Cooper & Dunham

(57) ABSTRACT

A myocardial analysis and monitoring method, comprising the steps of receiving a number of ECG signals relating to a heartbeat of at least one patient, converting the received number of ECG signals into three perpendicular ECG signals, determining an average heartbeat from the ECG signals, calculating a plurality of parameters related to a condition of each patient from the number of ECG signals, storing information representative of a value of the plurality of parameters related to the condition of each patient in storage, repeating the steps of determining the average heartbeat, calculating the plurality of parameters and storing the information for as long as ECG signals continue to be received or until the storage is full, displaying at least a portion of the stored information as a graphical display, the graphical display representing a trend of at least one of the plurality of parameters, analyzing the displayed trend of the at least one of the plurality of parameters, and displaying at least one result of the analysis.

44 Claims, 25 Drawing Sheets-

OTHER PUBLICATIONS

Mikael Dellborg and Karl Swedber, Dynamic QRS–Complex and ST–Segment Monitoring in Acute Myocardial Infarction During Recombinant Tissue–Type Plasminogen Activator Therapy, The American Journal Of Cardiology, Feb. 15, 1991.

Peter Lundin et al., Continuous Vectorcardiography in Patients with Chest Pain Indicative of Acute Ischemic Heart Disease, Cardiology, N. 81, pp. 145–156, May 14, 1992.

Rix et al., High Resolution ECG System for Micropotential Analysis and Shape Classification, Annual International Conference Of The IEEE Engineering In Medicine And Biology Society, vol. 13, No. 2 (1991).

"Vectorcardiographic monitoring to assess early vessel patency after reperfusion therapy for acute myocardial infarction", M. Dellborg et al., European Heart Journal, p. 21–29, (1995).

"Non–invasive risk stratification within 48h of hospital admission in patients with unstable coronary disease", K. Anderson et al., European Heart Journal, p. 780–788, (1997).

"A Clinical Introduction to the MIDA Concept Manual", 1993, pp. 5–36.

"The MIDA CoroNet Product Line, Product Information and Pricelist", Jun., 1993, pp. 3–21.

"MIDA 1200 CoroNet Central Unit", Aug., 1992.

"MIDA 1100 Bedside Patient Monitor", Aug., 1992.

"MIDA 1000 Operator's Manual", May 1989, pp. 1–111.

Working with Ischemic Patients, pp. 3–7.

"Operations Manual MIDA™ CoroNet Central", English Edition, Apr., 1994, vol. 4.0, pp. 3–45.

"Coronary Artery Disease", 1991, vol. 2, pp. 43–52.

"66th Scientific Sessions Abstract Form", Sven Hauck, Franz–Volhard–Klinik, American Heart Association, Nov. 8–11, 1993.

"Dynamic QRS Complex and ST Segment Vectorcardiographic monitoring can identify vessel patency in patients with acute myocardial infarction treated with reperfusion therapy", "American Heart Journal", M. Dellborg, E. Topol and K. Swedberg, Oct., 1991, vol. 122 pp. 943–948.

"Early Evaluation of Infarct Size by Vectorcardiographic Monitoring During the Early Hours of Acute Myocardial Infarction", European Society of Cardiology, S. Flochlay, P.G. Steg, JM. Juliard, D. Himbert, T. Laperche, R. Gourgon, Aug. 30–Sep. 1992.

"Dynamic Electrocardiographic Monitoring can Determine Early Vessel Patency After Reperfusion Therapy for Acute Myocardial Infarction", M. Dellborg, M. van den Brand, R. Dietz, S. Sen, M. Simoons, G. Steg, K. Swedborg on behalf of VERMUT–study. University of Goteborg, Goteborg, S.

Operations Manual MIDA™ Bedside, English Edition, Apr., 1994, vol. 4.0, pp. 3–71.

"User's Reference Manual to the MIDA™ System", English Edition, Jun. 1994, vol. 0.3, pp. 3–73.

"High Resolution ECG System for Micropotentials Analysis and Shape Classification", H. Rix, A. Varenne, A. Bally and E. Thierry, 1991, vol. 13, pp. 641–642.

"On Deriving the Electrocardiogram from Vectorcardiographic Leads", G.E. Dower, H.B. Machado, J.A. Osborne, Clinical Cardiology, 1980, vol. 3, 87–95.

"Acute Myocardial Infarction and Bundle–Branch Block–High Diagnostic Accuracy With Computerized Continuous, On–line Vectorcardiographic Monitoring", P. Eriksson, M. Dellborg, M. Riha, K. Swedberg, European Heart Journal, 1990.

Ischaemic Heart Disease and the Changes in the QRS and ST Segments During Exercise: "A Pilot Study With a Novel VCG System", Pilhall M, Riha M, Jern S, Clinical Physiology, 1992, vol. 12, pp. 209–223.

"Assessment of Reperfusion After Thrombolytic Therapy For Myocardial Infarction", Anita Zeiler Arnold, DO, and Eric J. Topol, MD, American Heart Journal, 1992, vol. 124, pp. 441–447.

"Changes in the QRS Segment During Exercise:—Effects of Acute Beta–Blockade with Propranolol", Pilhall M, Riha M, Jers S, Clinical Physiology, 1993, vol. 13, pp. 113–131.

"Impact of Early Thrombolysis on Chest Pain Score Reflecting Myocardial Ischemia in Relation to Various Markers of Ischemic Damage", J. Herlitz, M. Dellborg, M. Hartford, B. Karlson, T. Karlsson, International Journal of Cardiology, 1993, vol. 41, pp. 123–131.

"Ischemia—and Reperfusion—Induced Transient QRS–Vector Changes: Relationship to Size of the Ischemic Territory", Naslund U, Häggmark S, Johansson G, Reiz S, Cardiovascular Research, 1993, vol. 27, pp. 327–333.

"Quantification of Myocardium at Risk and Detection of Reperfusion by Dynamic Vectorcardiographic ST–Segment Monitoring in a Pig Occlusion—Reperfusion Model", Näslund U, Häggmark S, Johansson G, Reiz S, Cardiovascular Research, 1993, vol. 27, pp. 2170–2178.

"ECG Changes During Myocardial Ischemia, Differences Between Men and Women", J. Herlitz, MD, M. Dellborg, MD, H. Emanuelsson, MD, K. Swedberg, MD, Journal of Electrocardiology, 1994, vol. 27 (suppl).

"Prognostic Information From On–line Vectorcardiology in Acute Myocardial Infarction", Peter Lundin, MD, Sven V Eriksson, MD, Lars–Erik Stranberg, MD, and Nina Rehnqvist, MD, PhD, American Journal of Cardiology, 1994, vol. 74, pp. 1103–1108.

"Prognostic Information From On–line Vectorcardiology in Unstable Angina Pectoris", Peter Lundin, Sven V Eriksson, Mia Fredriksson, Nina Rehnqvist, Cardiology, 1995, vol. 86, pp. 60–66.

"Dynamic QRS–Complex and ST–Segment Monitoring in Acute Myocardial Infarction During Recombinant Tissue–Type Plasminogen Activator Therapy", Dellborg M, Riha M, Swedberg K, for the TEAHAT study–group, American Journal of Cardiology, 1991, vol. 67, pp. 343–349.

"Continuous Vectorcardiology in Patients With Chest Pain Suggestive of Acute Ischemic Heart Disease (IHD)", Peter Lundin, Sven V Eriksson, Nina Rehnqvist, Cardiology 1992, vol. 81, pp. 145–156.

"Dynamic Changes of the QRS Complex in Unstable Angina Pectoris", Dellborg M, Gustaffosson G, Riha M, Swedberg K, International Journal of Cardiology, 1992, vol. 36, pp. 151–162.

"Silent Myocardial Ischemia During Coronary Angioplasty", Mikael Dellborg MD, Håkan Emanuelsson, MD, Karl Swedberg, MD, Cardiology, 1993, vol. 82, pp. 325–334.

"Early Electrocardiographic Changes in Acute Myocardial Infarction Treated by Streptokinase or Alteplase: A Randomized Study With Dynamic, Multi–lead, Electrocardiographic Monitoring", Mikael Dellborg MD, Ann–Marie Svensson RN, Mats Johansson MD, Karl Swedborg MD, Cardiology, 1993, vol. 82, pp. 369–376.

"Electrocardiographic Assessement of Infarct Size: Comparison between QRS scoring of 12–lead Electgrocardiology and Dynamic Vectorcardiography", Mikael Dellborg, Johan Herlitz, Martin Risenfors and Karl Swedberg, International Journal of Cardiology, 1993, vol. 40, pp. 167–172.

"A Clinical Appraisal of the Vectorcardiogram in Myocardial Infarction. II The Frank System", Hugenholtz PG, Forkner CE Jr, Levine HD, Circulation, 1961, vol. 24, pp. 825–850.

"Correlation of Vectorcardiographic Criteria For Myocardial Infarction With Autopsy Findings", Gunner RM, Pietras RJ, Blackaller J, Damun SE, Szanto DB, Tobin JR, Circulation, 1967, vol. 35, p. 158–171.

"A Lead Synthesizer for the Frank System to Simulate the Standard 12–Lead Electrocardiogram", G.E. Dower, Journal of Electrocardiology, 1968, vol. 1, pp. 101–116.

"Comparative Quantitative Analysis of the Electrocardiogram and the Vectorcardigram", McConahay DR, McCallister BD, Hallerman FJ, Smith RE, Circulation, 1970, vol. 42, p. 245–259.

"Electrocardiogram and Vectorcardiogram in Myocardial Infarction", Levine HD, Young E, Williams RA, 1972, Circulation, vol. 45 p. 457–470.

"Vectorcardiographic Criteria for the Diagnosis of Anterior Myocardial Infarction", Starr JW, Wagner GS, Draffin RM, Reed JB, Walston A, Behar VS, 1976, Circulation, vol. 53, pp. 229–234.

"XYZ Data Interpreted by a 12–Lead Computer Program Using the Derived Electrocardiogram", G.E. Dower, Hilario Bastos Machado, J. Electrocardiogram. 1979, vol. 12, pp. 249–261.

"Comparative Accuracy of Electrocardiographic and Vectorcardiographic Criteria for Inferior Myocardial Infarction", Hurd II HP, Starling MR, Crawford MH, Dlabal PA, O'Rourke RA, 1981, Circulation, vol. 63, pp. 1025–1029.

"Sensitivity for Telemed Diagnosis of Myocardial Infarction by Use of 12–Lead Electrocardiogram Derived from Frank XYZ Leads", Bruce RA, Belanger L, Blackmon JR, Trimble S., Journal of Electrocardiology, 1982, vol. 15, pp. 157–163.

"Continuous Vectorcardiography in Acute Myocardial Infarction. Natural Course of ST and QRS Vectors", Sederholm M, Erhardt L, Sjögren A, International Journal of Cardiology, 1983, vol. 4, pp. 53–63.

"Relation Betwen ST and QRS Vector Changes and Myoglobin Release in Acute Myocardial Infarction", Sederholm M, Sylven C, Cardiovascular Research, 1983, vol. 17, pp. 589–594.

"Quantitative Assessment of Myocardial Ischemia and Necrosis by Continuous Vectorcardiography and Measurement of Creatine, Kinase Release in Patients", Sederholm M, Grottum P, Erhardt L, Kjekshus J, Circulation, 1983, vol. 5, pp. 1006–1012.

"Reduction of Infarct Size With the Early Use of Timolol in Acute Myocardial Infarction", The International Collaborative Study Group (Coordinator M. Sederholm), New England Journal of Medicine, 1984, vol. 310, pp. 9–15.

"The ECDG: A Derivation of the ECG from VCG Leads", Gordon E. Dower, Journal of Electrocardiology, 1984, vol. 17, pp. 189–191.

"Real–Time Serial Analysis of Infarctional Changes in the Vectorcardigan", Gröttum P. Computer and Biomedical Research, 1985, vol. 18, pp. 205–219.

"Course of Chest Pain and its Relation to CK Release and ST/QRS Vector Changes in Patients With Acute Myocardial Infarction Randomized to Treatment With Intravenous Timilol or Placebo", Sederholm M, GröP, Kjekshus J, Erhardt L, American Heart Journal, 1985, vol. 110, pp. 521–528.

"When is the Vectorcardiogram Superior to the Scalar Electrocardiogram?", Chou TC, Journal of the American College of Cardiology, 1986, vol. 8 , pp. 791–799.

"A Comparison of Cumulated CK Release With Three Vectorcardiographic Methods of Estimating Myocardial Infarct Size", Gröttum P, Kjekshus JK, Journal of Electrocardiology, 1986, vol. 19, pp. 337–345.

"Evolution of Vectorcardiographic QRS Changes During Myocardial Infarction in Dogs and in Their Relations to Infarct Size", Gröttum P, Mohr B, Kjekshus J, Cardiovascular Research, 1986, vol. 20, pp. 108–116.

"Comparison of the Classification Ability of the Electrocardiogram and Vectorcardiogram", Jos L. Willems MD, Emmanuel Lessaffre, Dsc, and Jos Pardaens Dsc., American Journal of Cardiology, 1987, vol. 59, pp. 119–124.

"Quantitative and Temporal Relation Between the Release of Myoglobin and Creatine Kinase and the Evolution of Vectorcardiogram Changes During Acute Myocardial Infarction in Man", Gröttum P, Sederholm M, Kjekshus K, Cardiovascular Research, 1987, vol. 21, pp. 652–659.

"Bundle–Branch Block and Acute Myocardial Infarction–Predictive Value of Initial ST Vector Magnitude", P. Erikkson, M. Dellborg, M. Riha, K. Swedberg, 1991, European Heart Journal, vol. 12, p. 666.

"Early ST–Segment Variability in Acute Myocardial Infarction Indicates a Large Infarction and is not Influenced by Treatment with Thrombolytics", M. Dellborg, K. Swedberg, European Heart Journal, 1991, vol. 12, p. 771.

"Changes of the QRS–Complex are More Sensitive than ST–Segment Devations in the Detection of Temporary Myocardial Ischemia During PTCA", S. Hauk, R. Lechenmayer, D. Höhnlein, K.J. Osterziel, R. Willenbrock, G. Claus, D. Gulba, R. Dietz, Circulation, 1993, vol. 88, p. 1636.

"Noninvasive Assessment of Reperfusion and Reocclusion After Thrombolysis in Acute Myocardial Infarction", Peter Klootwijk MD, Christa Cobbaert PhD, Paolo Fioretti MD, Peter Paul Kint RN and Maarten L. Simoons MD, American Journal of Cardiology, vol. 72, 1993, pp. 75G–84G.

"Computerized Vectorcardiography for Improved Perioperative Cardiac Monitoring in Vascular Surgery", Gannedahl PE, Edner M, Ljungqvist OH, Journal of the American College of Surgeons, 1996, vol. 182, pp. 530–536.

"The Image Surface of a Homogeneous Torso", Frank E., American Heart Journal, 1954, vol. 47, pp. 757–768.

"Absolute Quantitative Comparison of Instantaneous QRS Equipotentials on a Normal Subject with Dipole Potentials on a Homogenous Torso Model", Frank E., Circulation Research, 1955, vol. 3, pp. 243–251.

"An Accurate, Clinically Practical System For Spatial Vectorcardiography", Frank E., Circulation, 1956, vol. 13, pp. 737–749.

"The Importance of Derived 12–Lead Electrocardiography in the Interpretation of Arrythmias Detected by Holter Recording", Pablo Denes MD, American Heart Journal, 1992, vol. 124, pp. 905–911.

"Transient Exacerbation of ST–Segment Evaluation Upon Reperfusion in acute Myocardial Infarction", G. Steg, M. Dellborg, M. Simoons, Journal of Electrocardiology, 1994, vol. 26 (suppl), p. 156.

"Dynamic Vectorcardiographic Monitoring in the Coronary Care Unit—The Göteborg Experience", Ann–Marie Svensson, Mikael Dellborg, Karl Swedberg, European Heart Journal, 1991, vol. 12, p. 1579 (abstr).

"Comparison Using Dynamic Vectorcardiography and MIBI SPECT of ST–Segment Changes and Myocardial MIBI Uptake During Percutaneous Transluminal Coronary Angioplasty on the Left Anterior Descending Coronary Artery", P.G. Steg MD, M. Faraggi MD, PhD, D. Himbert MD, J–M Juliard MD, A. Cohen–Solal MD, R. Lebtahi MD, R. Gourgon MF and D. Le Guludec MD, American Journal of Cardiology, 1995, vol. 75, pp. 998–1002.

"Dynamic On–Line Vectorcardiography Improves and Simplifies In–Hospital Ischemia Monitoring of Patients With Unstable Angina" Mikael Dellborg MD, Klas Malmberg MD, Lars Ryden MD, FACC, Ann–Marie Svensson RN, Karl Swedberg MD, FACC, Journal of the American College of Cardiology, 1995, vol. 26, pp. 1501–1507.

"Minimal Influence of Anaesthesia and Abdominal Surgery on Computerized Vectorcardiography Recordings", P. Gannedahl, M. Edner, S.G.E. Lindahl and O. Ljungqvist, Acta Anaesthesiologica Scandinavica, 1995, vol. 39, pp. 71–78.

"Continuous Vectorcardiographic Changes in Relation to Scintigraphic Signs of Reperfusion in Patients with Acute Myocardial Infarction Receiving Thrombolytic Therapy", P. Juhlin, P–A Boström, O. Hansen, H. Diemer, M. Feitag, B. Lilja and L. Erhardt, Journal of Internal Medicine, 1996, vol. 259, pp. 35–41.

"Vectorcardiographic Monitoring to Assess Early Vessel Patency After Reperfusion Therapy for Acute Myocardial Infarction. The VERMUT Trial", M. Dellborg, P.G. Steg, M. Simoons, R. Dietz, S. Sens, M. van den Braud, U.Lotze, S. Hauck, R. van den Wieken, D. Himbert, A–M. Svensson and K. Swedberg, European Heart Journal, 1995, vol. 16, pp. 21–29.

"On–Line Computerized Vectorcardiography Monitoring of Myocardial Ischemia During Coronary Angioplasty: Comparison with 12–Lead Electrocardiography", S. Jensen, G. Johansson, G. Osterman, S. Reiz and Ulf Näslund, Coronary Artery Disease, 1994, vol. 5, pp. 507–514.

"Dynamic QRS–Complex and ST–Segment Monitoring by Continuous Vectorcardiography During Coronary Angioplasty", M. Dellborg, H. Emanuelsson, M. Riha and K. Swedberg, Coronary Artery Disease, 1991, vol. 2, pp. 43–52.

"Changes in QRS Segments During Exercise in Relation to Scintigraphic Myocardial Perfusion Defects: A Multivariate Analysis", M. Pilhall, L. Jarneborn, M. Riha and Sverker Jern, Current Science, 1993, vol. 4, pp. 87–99.

"Increased Rate of Evolution of QRS Changes in Patients With Acute Myocardial Infarction—Results from the Vermut Study", M. Dellborg, P. Gabriel Steg, M. Simoons, R. Dietz, S. Sen, M. van den Brand, U. Lotze, S. Hauck, J. Juliard and K. Swedberg, Journal of Electrocardiography, 1993, vol. 26, pp. 244–248.

"Dynamisk Kontinuerlig Vektokardiografi", J. Markenvard and M. Dellborg, Ugeskr Leger, 1992, vol. 17, pp. 2296–2300.

"Continuous Vectorcardiography in Cardiac Surgery: Natural Course of Vector Changes and Relationship to Myocardial Oxygen Uptake", O. Wesslen, R. Ekroth, P. Joachimsson, L. Nordgren, S. Nystrom and H. Tyden, Scand J. Thor Cardovascular Surgery, 1991, vol. 25, pp. 45–50.

"Myocardial Recovery After Cardiac Surgery: A Study of Haemodynamic Performance and Electrophysiolofy During the First 18 Postoperative Hours", O. Wesslen, J. van der Linden, R. Ekroth, P. Joachimsson, L. Nordgren and S. Nystrom, Journal of Cardiothoracic Anesthesia, 1990, vol. 6, pp. 672–680.

"Ischemia Detected by Continuous On–Line Vectorcardiographic Monitoring Predicts Unfavourable Outcome in Patients Admitted with Probable Unstable Coronary Disease", K. Anderson, P. Erikksson and M. Dellborg, Coronary Artery Disease, 1996, vol. 7, pp. 753–760.

"Exercise–induced QRS Changes in Health Men and Women: A Multivariate Analysis on their Relation to Background Data and Exercise Performance", M. Pilhall, M. Riha and S. Jern, European Heart Journal, 1992, vol. 13, pp. 1317–1324.

Vectorcardiographic Monitoring to Assess Early Vessel Patency After Reperfusion Therapy for Acute Myocardial Infarction. The Vermut Trial, M. Dellborg, P.G. Steg, M. Simoons, R. Dietz, S. Sens, M. van der Brand, U. Lotze, S. Hauck, R. van der Wieken, D. Himbert, A.–M. Svensson and K. Swedberg, European Heart Journal, 1995, vol. 16, pp. 21–29.

"Thrombin Inhibition with Inogatran for Unstable Angina Pectoris: Evidence for Reactivated Ischemia After Cessation of Short–Term Treatment", K. Anderson, M. Dellborg, H. Emanuelsson, L. Grip and K. Swedberg, Coronary Artery Disease, 1996, vol. 7, pp. 673–681.

"Calcualted 12–Lead ECG Derived from Vector ECG (Frank) as Compared with Traditionally Register 12–Lead ECG", E. Lofsjogard–Nilsson, Dep. of Clinical Physiology, Karolinska Hospital, Stockholm Sweden, Journal of Electrocardiology, 1990, vol. 23, p. 210.

"Ischemia Monitoring With On–Line Vectorcardiography Compared With Results From a Predischarge Exercise Test in Patients with Acute Ischemic Heart Disease", P. Lundin, J. Jensen, N. Rehnqvist and S. Eriksson, Journal of Electrocardiology, 1995, vol. 28. pp. 277–285.

"Tailored Thrombolytic Therapy", M. Simoons and A. Arnold, Circulation, 1993, vol. 88, pp. 2556–2564.

"Sleep Apnoea and Nocturnal Angina", K. Franklin, J. Nilsson, C. Sahlin and U. Näslund, 1995, vol. 345, pp. 1085–1087.

"Noninvasive Assessment of Speed and Stability of Infarct–related Atery Reperfusion: Result of the Gusto St Segment Monitoring Study", A. Langer, MD, FACC, M. Krucoff, MD, FACC, P. Klootwijk, MD, R. Veldkamp, MD, M. Simoons, MD, FACC, C. Granger, MD, FACC, R. Califf, MD, FACC, P. Armstron, MD FACC, for the Gusto Investigators, 1995, vol. 25, pp. 1552–1557.

"Electrocardiographic Evidence for Reperfusion–induced Ischemia after Thrombolysis of Direct Angioplasty for Acute Infarction", P.G. Steg, S. Flochlay, D. Himbert, JM. Juliard, R. Gourgon, 1992, European Herart Journal, vol. 13, p. 1093.

"Continuous Vectorcardiagraphy in Acute Myocardial Infarction", M. Sederholm, M. Riha, L.R. Erhardt, 1985, pp. 171–174.

"SUTIL: Intelligent Ischemia Monitoring System", J. Vila, J. Presedo, M. Delgado, S. Barro, R. Ruiz, F. Palacios, 1997, pp. 194–214.

4 ELECTRODES
(ALL EXCEPT V LEAD)

MYOCARDIAL ISCHEMIA AND INFARCTION ANALYSIS AND MONITORING METHOD AND APPARATUS

This application is a continuation-in-part application of U.S. Ser. No. 09/040,876, filed Mar. 18, 1998, now U.S. Pat. No. 6,038,469, which is a continuation-in-part application of U.S. Ser. No. 08/653,448, filed May 24, 1996, now U.S. Pat. No. 5,819,741 issued on Oct. 13, 1998 which is a continuation-in-part application of U.S. Ser. No. 08/320,511, filed Oct. 7, 1994, now U.S. Pat. No. 5,520,191, issued on May 28, 1996.

BACKGROUND OF THE INVENTION

(1) Field of the Invention

The present invention relates to cardiac monitoring and telemedicine systems and, more particularly, to cardiac monitoring systems which provide an analysis and display of one or more parameters relating to the condition of ischemic patients.

(2) Description of the Related Art

A number of new clog dissolving agents presented by the pharmaceutical industry during the past couple of years have given cardiologists the ability to immediately treat acute myocardial ischemia through chemical thrombolytic therapy. However, it is frequently difficult to properly control and adjust such therapy during the acute phase of a myocardial ischemia. Known methods are either expensive or have too large a delay (up to several hours) between the time of the myocardial ischemia time and the presentation of the results.

Some cardiac monitoring systems and methods also utilize a known 12-lead electrocardiogram in which electrocardiogram (ECG) signals are displayed directly on a monitor in real-time. Such a 12-lead ECG arrangement has the disadvantages that a large number of electrodes must be placed on the patient in positions which cover mainly the frontal parts of the myocardium. A large storage capacity is also required in order to record all the ECG signals from the electrodes. However, many doctors are familiar with the format of the 12-lead ECG.

Further, the normal procedure in the case of serious illness is to transport the patient to a hospital for diagnosis and treatment of the illness. However, it has proved to be advantageous to arrange for the nursing or ambulance staff to carry out the diagnosis and to start the treatment already at the place of patient pick-up. Such an arrangement likewise makes it possible to establish at an early stage whether a particular specialist competence and special equipment or the like are required, whereafter the patient may be transported straight to the place where such competence, equipment etcetera are available.

Such early diagnosis and treatment would be considerably facilitated, were the nursing staff given a possibility to carry with them a portable telemedicine device adapted to register signals from ECG and vector electrocardiogram (VCG) units and similar sensing equipment. A portable unit of this kind, which may be docked and thus be connected to a stationary communications network (LAN), which allows connection thereto of external measurement equipment, and which comprises a display device for visualization of the measurement results, is disclosed in U.S. Pat. No. 5,375,604.

However, this prior-art device is merely a passive unit and it is designed for reception and visualization only of signals from the measurement equipment. It cannot be used to establish active contact with and an exchange of information between the patient-attending staff and other individuals, a possibility which could be helpful in the diagnosis procedure as well as for the implementation of correct treatment measures. This is true particularly in the case of the above portable unit when used un-docked, in which case there is no communication with other equipment.

Furthermore, U.S. Pat. No. 5,441,047 describes a system according to which selected data on the patient is collected automatically, whereupon said data are forwarded via a stationary telecommunication network, such as a cable television network, to a centre where the diagnosis, monitoring or similar operations may be performed. The referred-to equipment is not, however, portable and in addition it comprises a plurality of independent components, and consequently this equipment is not adapted for ambulatory use and positioning onboard e.g. an ambulance. Nor is it adapted for active exchange of information between the nursing staff by the patient's side and the personnel at the central unit.

In addition, there is a need for message exchanges between the nursing staff by the patient's side and the personnel at the central unit as well as for possibilities of filling in certain types of pre-defined forms, such as patient case record files, already in the initial stage by the patient's side. These needs are not met in the prior-art devices.

In addition, it would be desirable to enter data manually and preferably by one hand only, in a convenient, rapid and simple manner. It likewise would be desirable, to construct the entry means sufficiently small so as not to make the portable equipment unnecessarily bulky and unmanageable.

SUMMARY OF THE INVENTION

The present invention constitutes a substantial improvement in cardiac monitoring systems, and in particular, an improvement in cardiac monitoring systems providing an analysis and display of parameters relating to the condition of ischemic patients.

A myocardial analysis and monitoring method comprises steps of receiving a number of ECG signals relating to a heartbeat of at least one patient, converting the received number of ECG signals into three perpendicular ECG signals, determining an average heartbeat from the ECG signals, calculating a plurality of parameters related to a condition of each patient from the number of ECG signals, storing information representative of a value of the plurality of parameters related to the condition of each patient in storage, repeating the steps of determining the average heartbeat, calculating the plurality of parameters and storing said information for as long as ECG signals continue to be received or until the storage is full. At least a portion of the stored information is displayed as a graphical display, the graphical display representing a trend of at least one of the plurality of parameters. The displayed trend of the at least one of the plurality of parameters can be analyzed and at least one result of the analysis displayed.

The analyzing step may include detecting episodes, each episode comprising a predetermined number of trend values above a predetermined upper threshold level or below a predetermined lower threshold level occurring within a predetermined period of time of each other. The number of detected episodes can be displayed.

The analyzing step may include detecting an amount of time for a parameter to decline from a maximum value to a predefined value and displaying the detected amount of time. The detected amount of time may begin at a start of a patient therapy.

The analyzing step may include detecting an amount of recovery of a parameter at a predetermined time and displaying the detected amount of recovery.

DETAILED DESCRIPTION OF THE PREFERRED EMBODIMENTS

Figure 7:
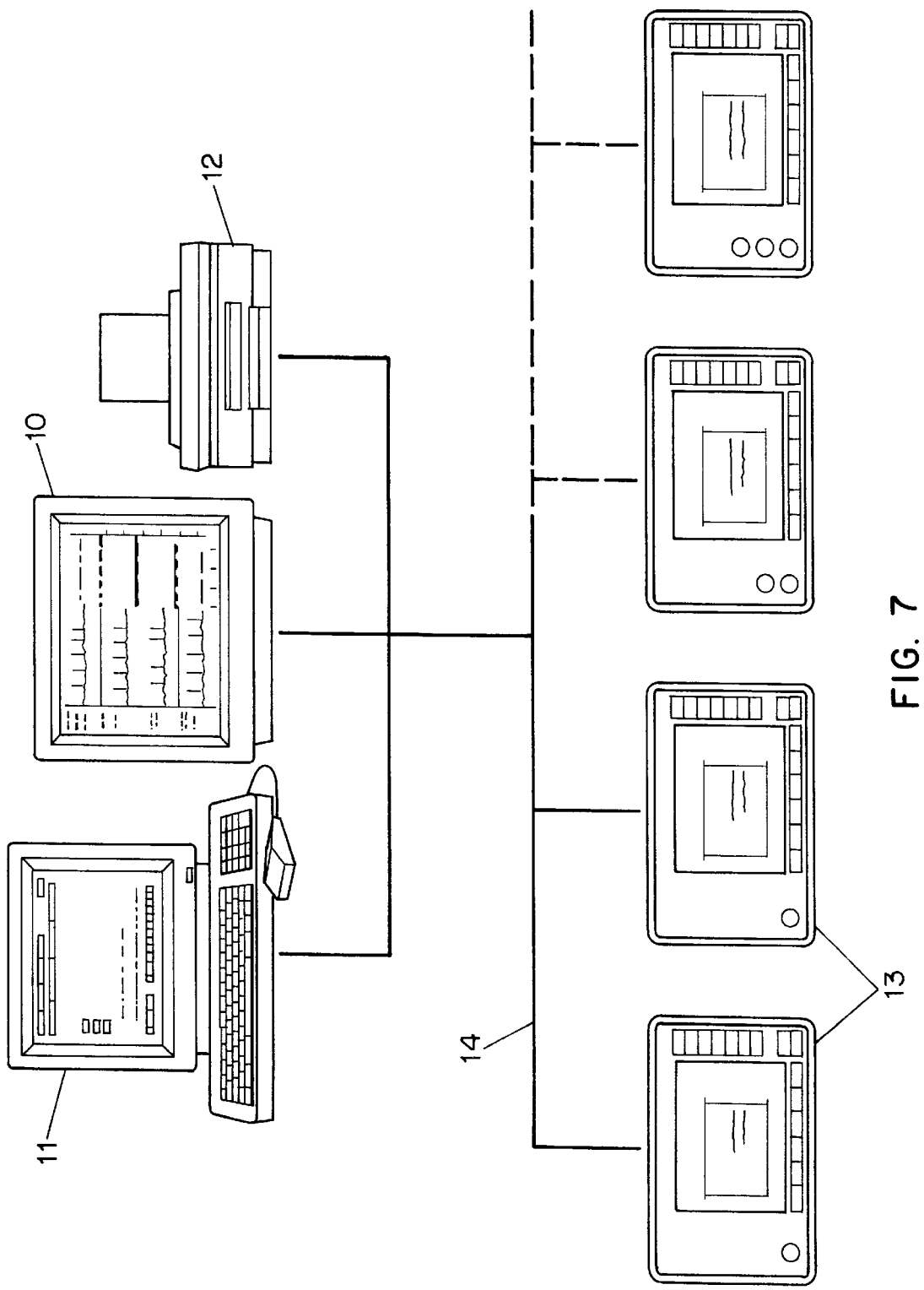
FIG. 7 is a diagram illustrating elements of the system in a first embodiment of the invention.

The system of a first embodiment of the invention is shown in FIG. 7. It consists of at least one central monitoring unit 10, a central workstation 11 for controlling the system, including the display on the central monitoring unit(s), and for storing data, a laser printer 12 and a plurality of bedside monitors 13, one for each patient. All of the units communicate via a network such as an Ethernet network 14.

Processing functions are divided between central workstation 11 and each bedside monitor 13. The distributed intelligence ensures maximum system reliability and offers both powerful traditional monitoring and advanced ischemia monitoring.

Figure 12:
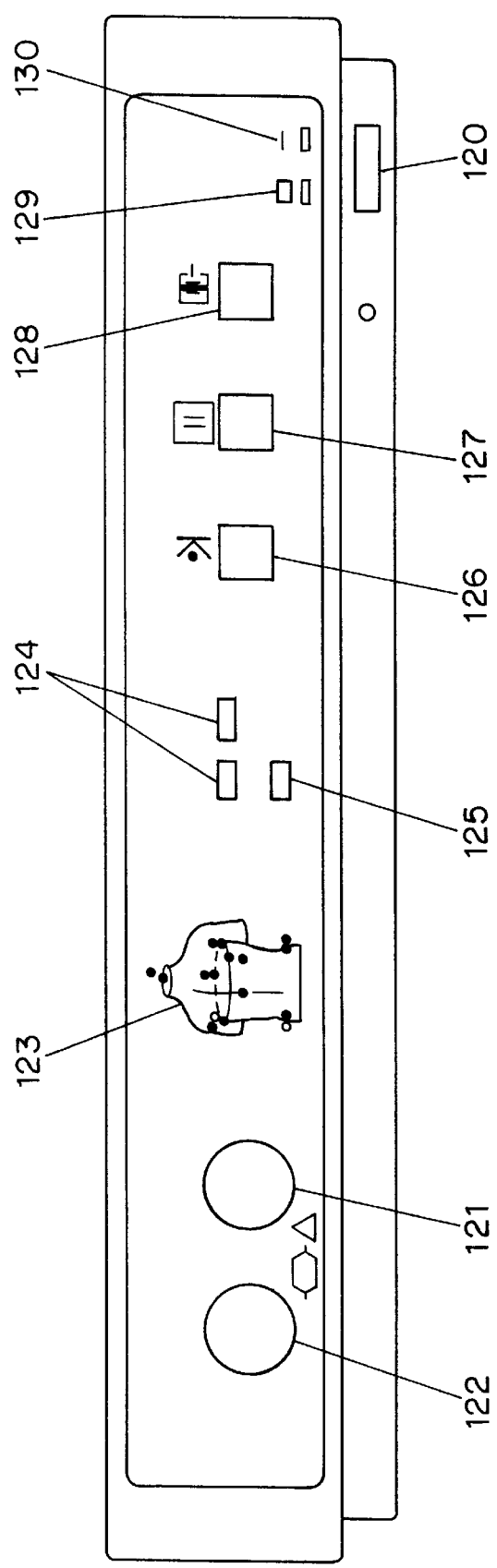
FIG. 12 shows the front face of an acquisition module used in another embodiment of a system employing the invention.

Each of the bedside monitors 13 combines multilead arrhythmia analysis with new, advanced ischemia monitoring features and does all the calculations for the ECG analysis, presents the information on the display and transmits it over Ethernet network 14 to a central processing unit in the workstation 11. Further, the bedside monitors 13 continuously store the three perpendicular leads, X, Y and Z, which can be used to study past events such as arrhythmia events. The past events which can studied are from the 12-lead and/or VCG in on-line mode, that is when the patient is connected to the system, or in review mode, that is when the patient is disconnected and discharged from the monitoring system. FIG. 12 shows the front face of an exemplary bedside monitor 13. In addition to the ECG analysis, each bedside monitor 13 is also available with a number of options, such as non-invasive blood pressure, pulse oximetry, dual invasive pressures and dual temperatures, and is operated simply by touching the self-instructive menus on the front of the monitor. Analogue ECG outputs on the back of the bedside 15 monitors allow connection to other medical equipment.

Eight ECG leads are used for improved sensitivity of the analysis of both arrhythmias and ischemia. With information from all eight leads, the ischemia analysis is able to reflect ischemic changes from the entire myocardium. The ischemic evolution over time is presented in a trend graph that is continuously updated on the display. The trend graph may include up to 8 days of continuous monitoring. With four traces and a trend graph, a waveform may be displayed for every physiological parameter in addition to the vital trend graphs. (For patients without ischemic symptoms, 4 leads can be used for monitoring.) The averaged beats in the form of the X, Y and Z leads are automatically calculated and stored every minute. From these signals a derived 12-lead ECG may be reviewed on the bedside monitor at any time during the monitoring session.

The central workstation can automatically identify up to six different functions (MIDA, HR/PVC, spo$^2$, NIBP, IBP and Temp for example) in each bedside monitor and all of the physiological information acquired by the bedside monitors can be transferred for examination and storage at the workstation. The monitoring functions controllable by the central workstation will thus vary depending on the configuration of the bedside monitors connected to the central workstation. For example, central workstation 11 may provide conventional ECG monitoring, arrhythmia monitoring, ischemia monitoring with parameters reflecting the ECG changes in clear trend graphs, averaged derived 12-lead ECG display, 24-hour full disclosure arrhythmia of all monitored patients, 24-hour continuous 12-lead ECG display derived from the continuously stored X, Y, and Z leads for all monitored patients and monitoring of any and all non-ECG functions monitored on the bedside monitors such as spo$^2$, NIBP, BP and Temp.

Figure 8:
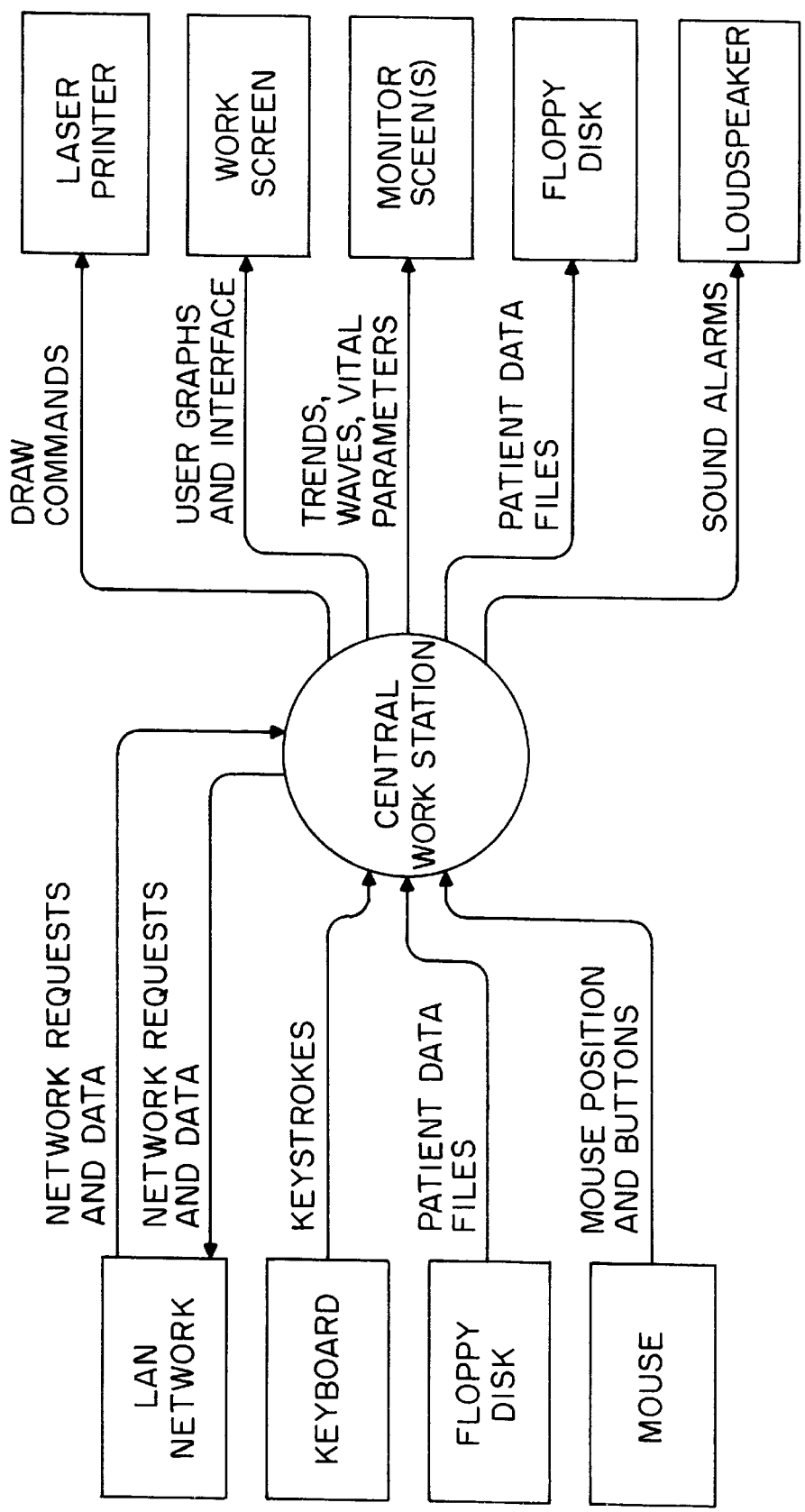
FIG. 8 is a block diagram graphically illustrating the connection of the central workstation to other components of an apparatus employing the invention.
Figure 13:
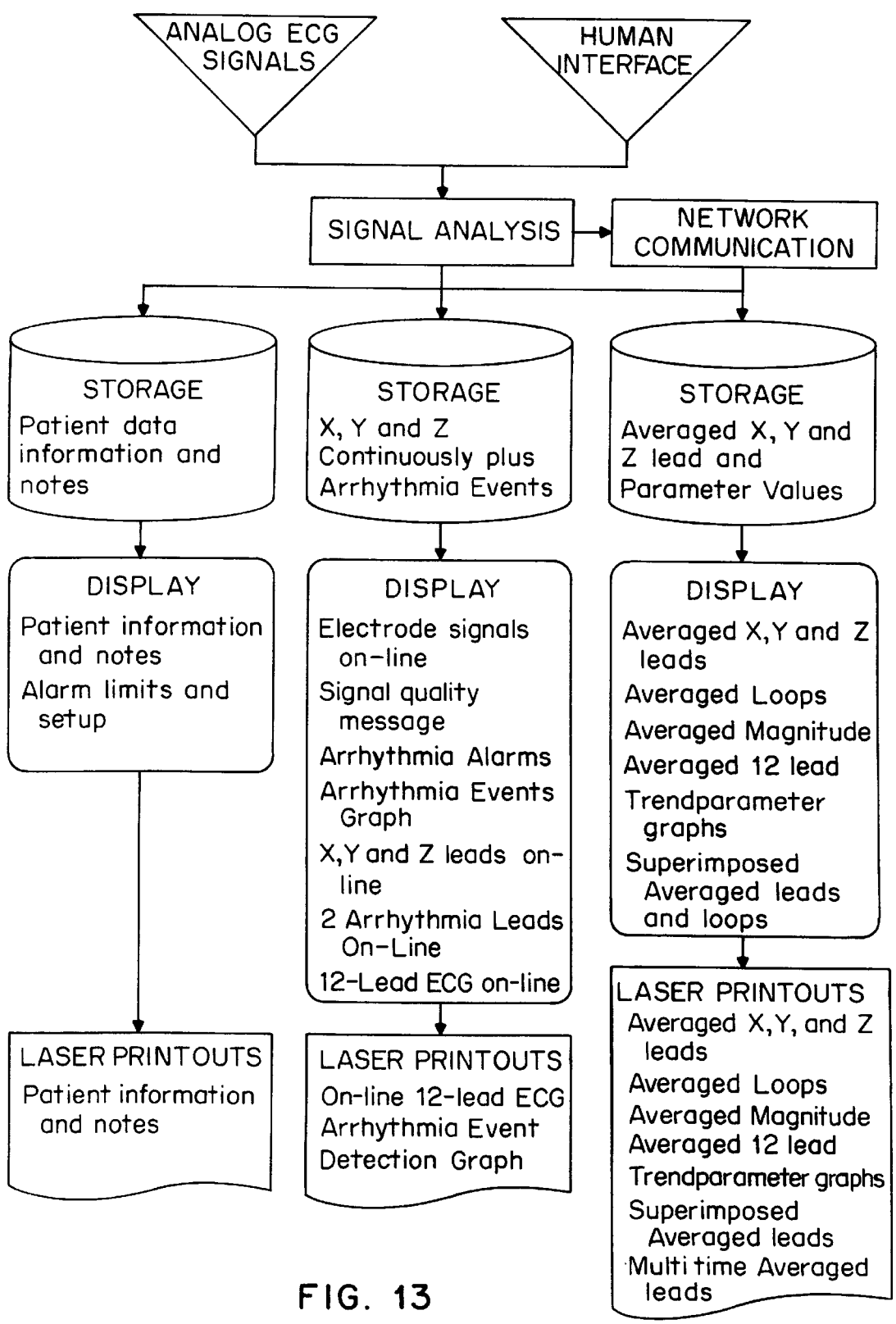
FIG. 13 shows the overall input/output possibilities in an apparatus employing the invention.

The central workstation preferably is a networking personal computer operating with specialized menu-driven applications software. An exemplary connection of the central workstation to other components is shown in FIG. 8 and an exemplary illustration of the functions which may be performed is shown in FIG. 13. The central workstation provides a straightforward and simple user interface operated through the selection of "keys" in a graphical display. Each key has an instructive text or symbol describing the function of the key. A mouse (or other pointing device) is used to point to and select a desired key. (In the examining functions, the mouse is also used to point out the ECGs to be enlarged, etc.) The surface of a key normally is grey. However, active keys are yellow and void keys that cannot be accessed are dark grey.

Figures 9, 10:
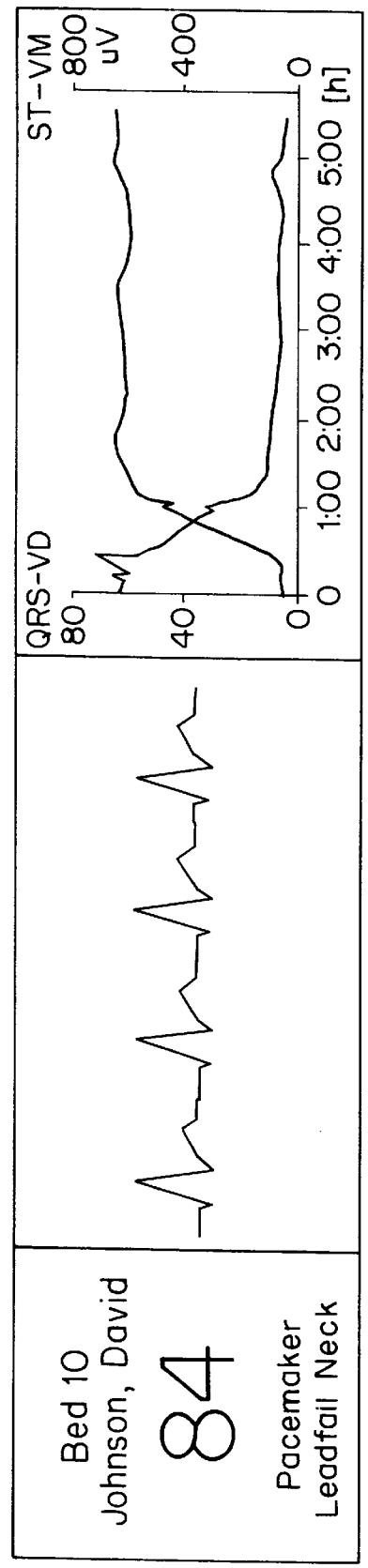
FIG. 9 is a diagram showing the top part of a graphical interface display which appears on the central workstation of a system employing the invention.
FIG. 10 is a diagram showing an example of the display format used for monitoring each patient on a central monitoring unit.
Figure 11:
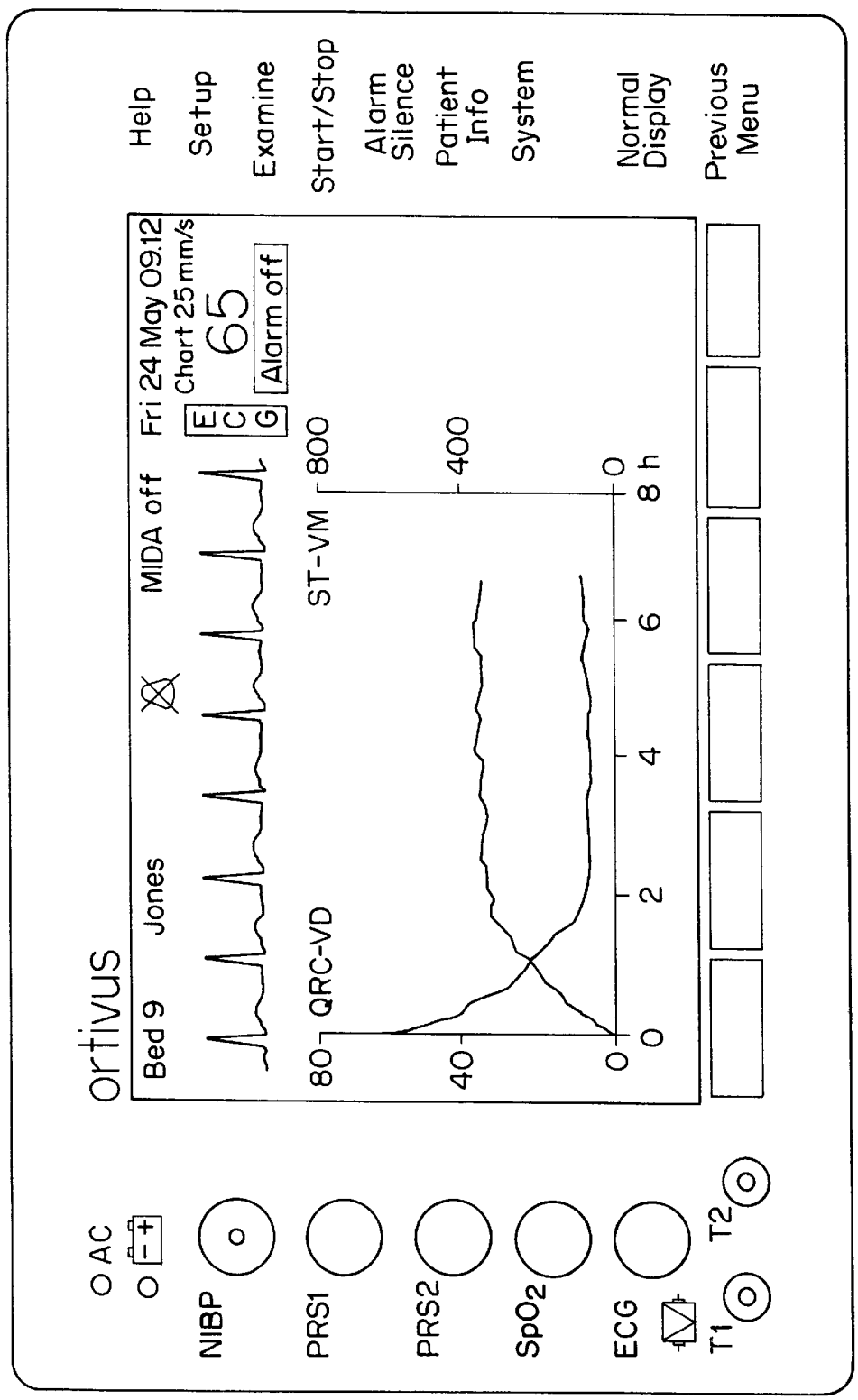
FIG. 11 shows the front face of a bedside monitor used in a first embodiment of a system employing the invention.

FIG. 9 shows an example of the initial menu displayed in an upper portion of the display in a preferred embodiment of the invention. There are two rows of keys. The keys in the top row are labeled with numbers corresponding to each one of a number of patients, System, Signal Status and Stored Patients. The lower row of keys preferably contains key commands for examining a patient file. For example, the keys may be labeled as Patient Info, Alarm, Report, Trend, ECG & VCG, Arrhythmia Events, ECG MIDA, ECG Review, All Leads and Setup. The keys are used to select and control all functions, both on the central monitors and on the workstation itself.

Signal status messages are displayed on the display of the workstation if no central monitor is in use. (Otherwise, signal status messages are always displayed on the central monitor.) A red patient key is used to indicate that something is wrong, that there is bad signal quality or problem with the analysis or other errors. If so, the reason may be seen in the Signal Status function. A crossed over key is used to indicate that the analysis has paused. The actual message for a specific patient is then displayed to the right of the patient name in the upper part of the workstation display.

Central Monitoring Units

All parameters available to the central workstation may be displayed as trend graphs on one or more central monitoring units 10. The central monitoring unit(s) 10 display the "live" situation of a plurality of patients simultaneously. The central monitoring units are preferably large (e.g., 17- or 21-inch), high-resolution computer monitors such as that shown in FIG. 7. Software display drivers in the workstation utilize high resolution graphics and the display preferably is at least 1024×768 pixels resolution. The monitors may continuously and simultaneously monitor ECG waveforms, vital parameters, alarms and vital ischemia trendings for each of a number of patients.

Arrhythmia alarms are presented in red letters on the displays and a 24-hour full disclosure arrhythmia review function offers complete control and documentation of all arrhythmias. The central monitoring unit(s) 10 also enable examination of derived 12-lead ECGs of every minute monitored. All other functions are displayed and controlled on the workstation.

The information on the monitors is fixed in order to always present the current status of all patients. All interactive functions and examination of patient data which appears on the monitors is controlled from the workstation. The left half of the monitor screen presents conventional monitoring including heart rates and patient information, waveforms, arrhythmia alarms and optional vital signs while the right-hand side presents the ischemia trends. The graphs display the ischemic evolution of each monitored patient starting from a designated time, such as the patient's admission. The graphs are continuously updated to always include the most recent values. Up to six patients may be monitored on each display. When more than four patients are monitored, additional monitors may be used. The network 14 allows the selection of any two waveforms from each bedside patient monitor to be displayed on the central monitor. The waveform selected to be displayed on the central monitor need not be the same waveform selected for display on the corresponding bedside monitor 13. An example of a trend graph displayed on the central monitor for a single patient is shown in FIG. 10. The signal status and MIDA messages are identical to the ones displayed in the Signal Status overview of the display for the central workstation discussed later.

The content of the display of a respective patient on the central monitors (leads, filters, size and speed) is selected by central workstation 11 in the manner described below. The same information is always displayed at the same location in the display for improved functionality. The left side of the display contains bed number 101, patient name 102, heart rate 103, pacemaker information 104 and signal status message 105. The right side of the display contains trend graph(s) 106 and MIDA recording status message 107.

A patient is chosen for monitoring by clicking the number key corresponding to the patient in the top row of keys on the Workstation.

The Setup Menu key is selected to adjust the patient's display. If the Monitored ECG Lead key of the Setup Menu is selected, then a picture is displayed which contains the waveform for each of the patient leads along with a respective corresponding key, as well as keys for selecting the filtering, curve size and sweep speed of the displayed waveforms. If waveforms other than ECG leads, such as Spo2 and PA pressure, are monitored, then these appear in the display as well and are controlled in the same manner as the ECG leads. The primary waveform to be displayed on the central monitor is selected by clicking the corresponding key.

The setup menu in the first embodiment displays three filter keys which enable the displayed waveform to be filtered for improved visual impression. The first key, "None", displays the waveform unfiltered. The second key is labeled "0.05–100 Hz" and gently filters the curve from baseline variations below 0.05 Hz and noise above 100 Hz.

The third key is labeled "0.5–40 Hz" and filters the displayed curve from baseline variations below 0.5Hz and noise above 40 Hz. The setup menu in the preferred embodiment also displays three ECG size keys which set the size of the displayed waveform. When the "Auto" key is selected, the size of the displayed curve is continuously adopted to fill two thirds of the height available for the curve. The adoption is very slow so that if the original amplitude of the curve slowly decreases (maybe due to necrosis), the automatic adoption may result in an unaffected curve on the monitor. The "10 mm/mV" key sets the amplitude of the displayed curve to 10 mm/mV. The "20 mm/mV" key sets the amplitude of the displayed curve to 20 mm/mV.

All curves on the central monitor have the same speed. The speed may be set to 25 mm/sec or 50 mm/sec via selection of the appropriate key.

For all patients, a second monitoring curve (additional ECG, pulseoximetry or pressure) may also be selected for display in addition to the primary curve. This function is controlled by selection of a key marked "On/Off" which appears under the header "2nd wave" in the setup menu display. Selecting the On/Off key activates the second curve. A key marked "Wave 1" is selected to enable control of the upper curve (lead, filter, etc.). A key marked "Wave 2" is selected to enable control of the lower curve.

The Patient Info key allows inputting of the patient's name, ID, original symptoms and physician comments. The information is entered on respective lines using the keyboard in typewriter fashion and then pressing the enter key. The Patient Info menu also contains a Pacemaker key which is selected to indicate that the patient has a pacemaker.

The menu also has an Add note feature which permits the entering of notes and observations at the workstation at any time. When the Add note key is selected, a field is opened at the bottom of the display, the time is automatically displayed, and the Add note key is changed to a save note key. The text of the note is entered and edited using the keyboard.

The note is saved by clicking on the Save Note key. If the patient's waveforms are stored for subsequent analysis, the system stores all notes as well. They may be reviewed and printed on paper at any time.

The Patient Info menu is closed by selecting either a Save Patient Info key or a Cancel key. When a patient is discharged from the bedside monitor, the central workstation stores all recordings, including 24-hour full disclosure arrhythmia, by default until the storage capacity is needed for new recordings. When capacity is full, the oldest recordings will be erased automatically.

Once the patient has been entered into the system as described above and the display for the central monitor has been formatted as described above, the system then commences on-line myocardial ischemia dynamic analysis and monitoring (MIDA) for treating patients with myocardial infarction, unstable angina or when monitoring patients during and post-PTCA.

Figure 4:
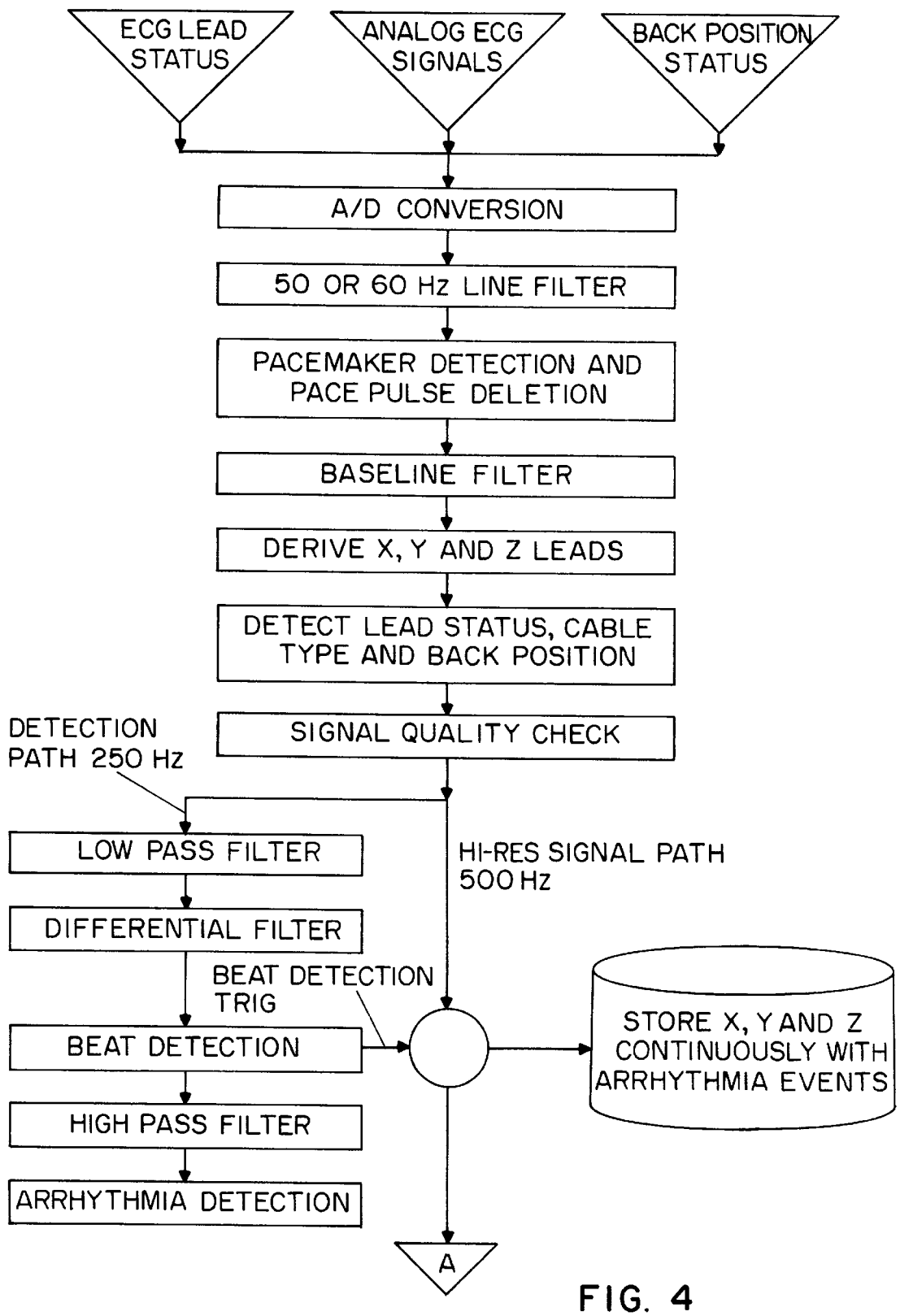
FIG. 4 is a flowchart depicting the manner in which three perpendicular leads (X, Y, and Z) are produced in a preferred embodiment of the invention.

Based on the electrical signals from eight ordinary surface ECG electrodes placed according to Frank, three perpendicular leads (X, Y, and Z) are produced in the manner shown in FIG. 4. The method used in the system permits ischemia monitoring based on Frank leads, analyzing the X, Y, and Z signals to achieve unique parameters, such as ST-VM, QRS-VD and STC-VM, which are displayed in a trend chart.

Figure 5:
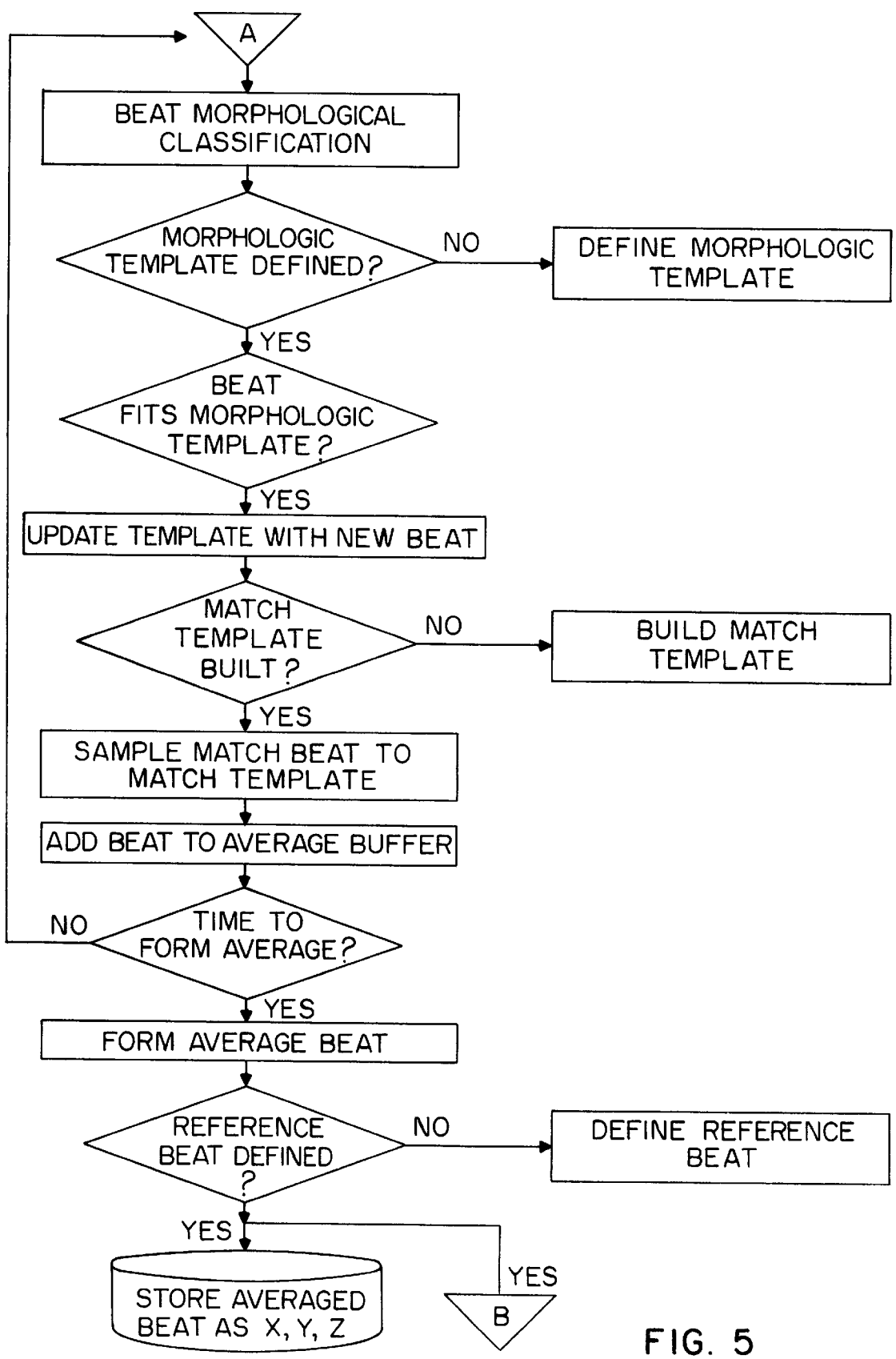
FIG. 5 is a flowchart showing the initial steps in the analysis and monitoring used in the preferred embodiment of the invention.

When monitoring starts in the manner shown in FIG. 5, beats undergo a morphological classification and a morphologic template is defined. If a beat fits the morphologic template, a match template is built, such by selecting a normal ECG beat to serve as the template. Beats are compared to the match template to determine which beats are "normal" beats that should be included in the analysis and which beats should be excluded from the MIDA analysis. During the remainder of the analysis, the three leads X, Y and Z are continuously scanned for "normal" beats. When a normal beat is found, it is matched and included in an average of the acquired normal beats formed at even time intervals, preferably every minute provided that the quality of the signal is sufficient. The ECG from the first average beat is referred to as the Reference Complex and used as a reference to which the ECGs from all subsequent beats are compared to see the relative change over time.

Figure 6:
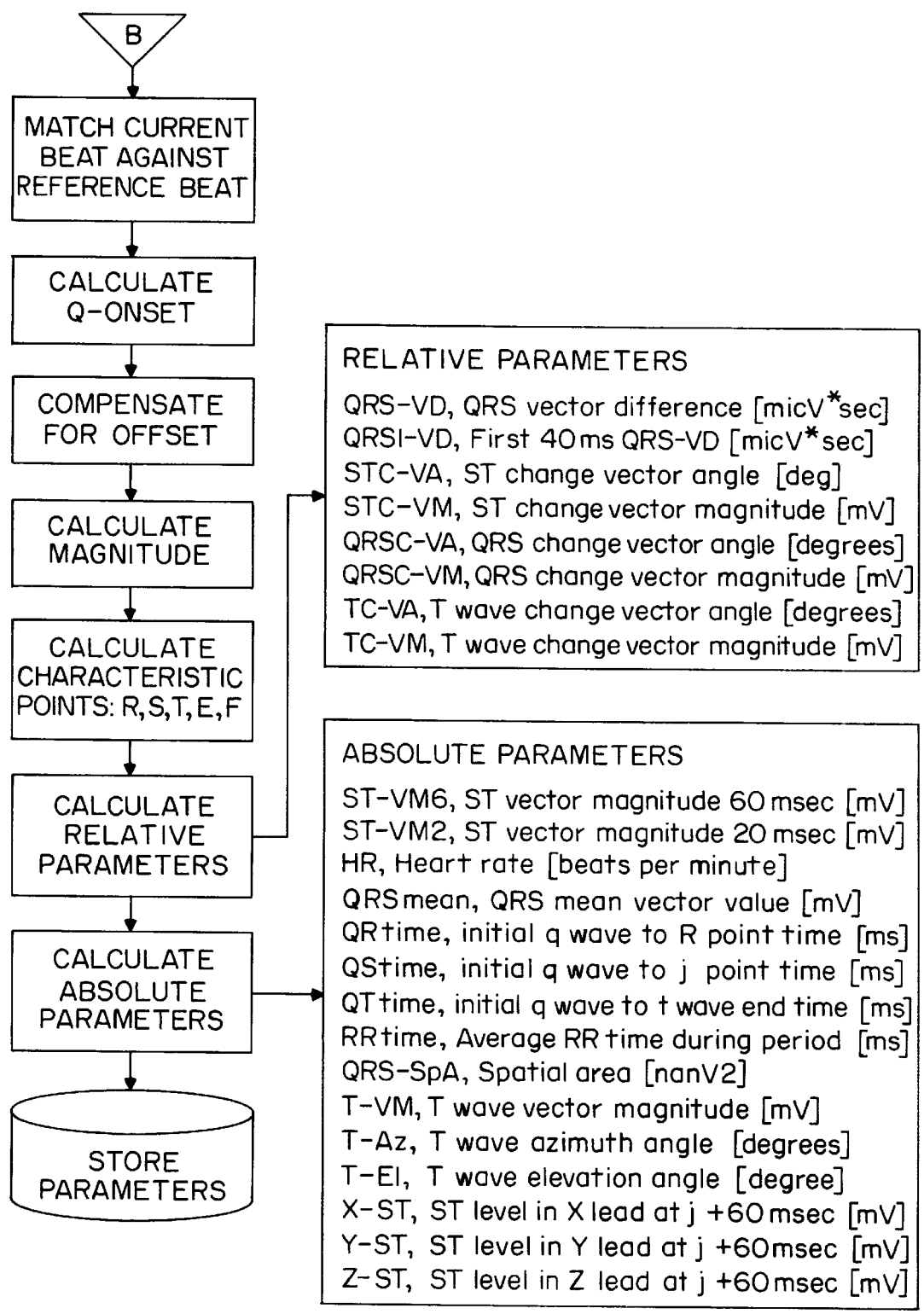
FIG. 6 is a flowchart depicting the manner in which the averaged beat, represented by the averaged X, Y and Z leads, undergoes advanced calculations to determine parameters describing the condition of the ECG.

At even time intervals between a range of 10 seconds and 4 minutes, the averaged beat, represented by the averaged X, Y and Z leads, undergoes advanced calculations as shown in FIG. 6 to determine one or more parameters up to thirty different parameters describing the condition of the ECG. The parameters are stored in addition to the 5 averaged ECG itself.

There are two kinds of parameters: absolute and relative. Absolute parameters are calculated from the actual ECG complex itself. Relative parameters are calculated from the difference between the current ECG complex and the initial reference complex to reflect serial changes over time.

The following are examples of absolute parameters: QRSmax, QRSmean, ST-VM, ST-VM2, X-ST, Y-ST, Z-ST, QRS-SpA, HR, QRtime, QStime, QTtime, RRtime, T-VM, T-Az, T-El, X-ST, Y-ST, Z-ST and Abnorm.

QRSmax (mV) is the maximum magnitude within the QRS-complex.

QRSmean (mV) is the mean magnitude of the ECG-vector during the time ranging from QRS onset up to QRS end of the initial QRS-complex.

Figure 2:
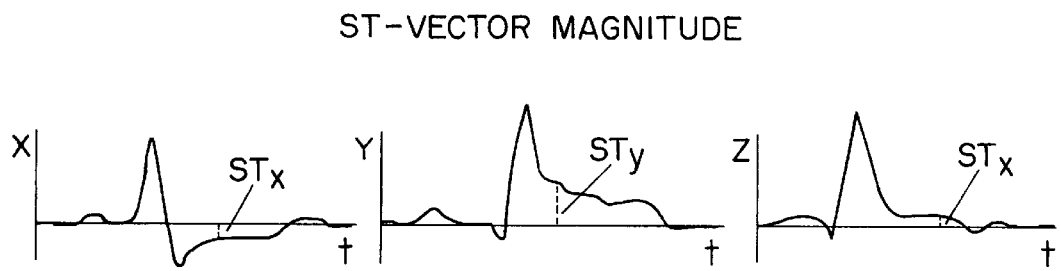
FIG. 2 is a graphical representation illustrating the ST-VM parameter.

The ST vector magnitude (ST-VM) measures the total offset of the ST-segment and is commonly accepted as a measure of ischemia in the myocardium during ischemia. It is measured in every averaged beat, 60 milliseconds after the J point (the end of the QRS complex). The values from the X, Y and Z leads are fed into the formula:

$$ST\text{-}VM = Sqrt(ST_x^2 + ST_y^2 + St_z^2) \qquad (1)$$

and the resulting ST-VM value is plotted in the trend graph. The way the formula is constructed, an ST elevation in one lead does not neutralize an ST depression in another lead. Both elevations and depressions are detected simultaneously. See FIG. 2. Since the ST segment is measured in both the X, Y and Z leads, it provides one ST measure that covers the entire heart.

ST-VM2 (mV) is the ST vector magnitude 20 ms after the J point.

X-ST (mV) is the ST level in the X lead 60 ms after the J point.

Y-ST (mV) is the ST level in the Y lead 60 ms after the J point.

Z-ST (mV) is the ST level in the Z lead 60 ms after the J point.

QRS-SpA (nanv$^2$) is the area in the space drawn by the ECG-vector from the point of the initial QRS onset to QRS end. HR (beats per minute) is the mean value of the heart rate during the MIDA interval.

QRtime (ms) is the time between QRS onset and the maximum magnitude of the current complex.

QStime (ms) is the time between QRS onset and QRS end of the current complex.

QTtime (ms) is the time between QRS onset and the maximum magnitude within the T wave of the current complex.

RRtime (ms) is the mean value of the RR intervals during the averaging period.

The T vector magnitude (T-VM) measures the maximum magnitude within the T-wave of the current complex in mV. The ECG-vector in this point is called the T-vector.

T-Az is the angle of the T-vector in the transversal plane, 0 to 180 degrees from sinister to dexter, and positive if anterior and negative if posterior.

T-El is the angle of the T-vector from the vertical axes, 0 to 180 degrees from dist to cranium.

Abnorm is the number of abnormal beats during the averaging period. All beats that are not classified into the reference class are labeled abnormal.

Figure 3:
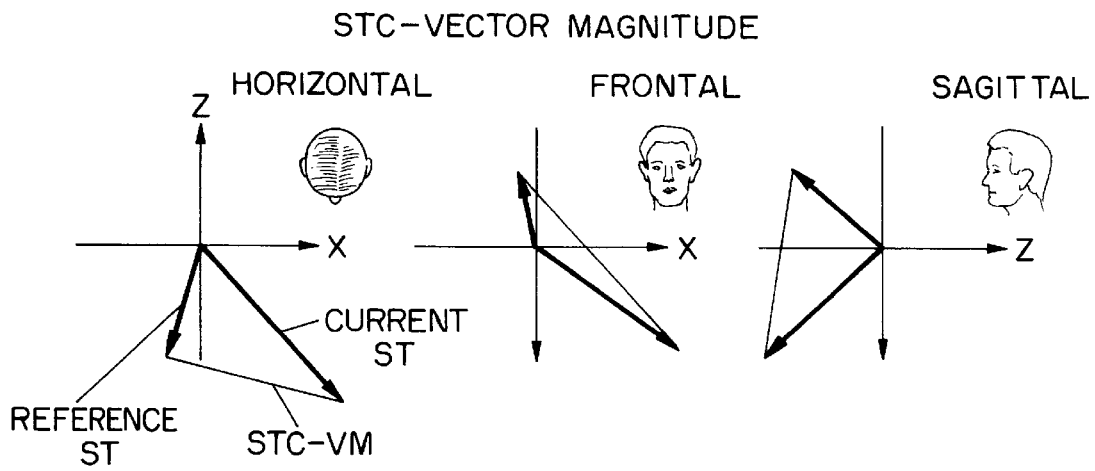
FIG. 3 is a graphical representation illustrating the STC-VM parameter.

The change of the ST magnitude compared to when monitoring was 15 started (STC-VM) is also calculated as shown in FIG. 3. The ST differences are fed into the formula:

$$STC\text{-}VM = Sqrt(STC_x^2 + STC_y^2 + STC_z^2) \quad (2)$$

Figure 1:
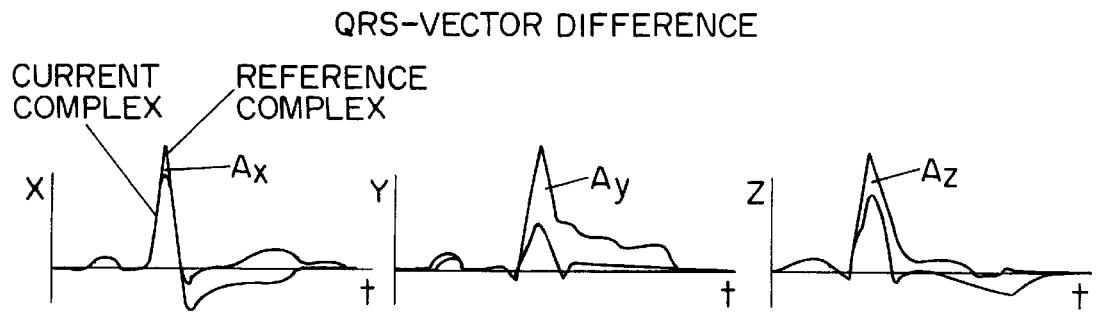
FIG. 1 is a graphical representation illustrating the QRS-VD parameter.

The following are examples of relative parameters: QRS-VD, QRSI-VD, QRSA-VA, QRSC-VM, STC-VA, STC-VM, TC-VA and TC-VM. The QRS vector difference (QRS-VD) measures changes in the QRS complex compared to the initial ECG and reflects the change in morphology of the QRS complex caused by, e.g. necrosis and temporary ischemia compared to when monitoring was started. The complex is compared to the initial QRS complex and the arial difference (A in FIG. 1) is calculated in the X, Y and Z leads. The values are fed to the formula:

$$QRS\text{-}VD = Sqrt(A_x^2 + A_y^2 + A_z^2) \quad (3)$$

and the resulting QRS-VD is plotted in the trend graph.

QRSI-VD (mVs) is the initial QRS vector difference which is the same as for QRS-VD except that the areas $A_x$, $A_y$ and $A_z$ range from QRS onset of the initial QRS complex and 40 ms forward.

QRSC-VA is the QRS vector angle change and represents the change in the angle between the current and initial QRS vectors.

QRSC-VM (mV) is the QRS vector magnitude change and represents the distance between the initial and current QRS vectors.

STC-VA is the ST vector angle change and represents the change in the angle between the initial and current ST vectors.

STC-VM (mV) is the ST vector magnitude change and represents the distance between the initial and current ST vectors.

TC-VA is the T vector angle change and represents the change in the angle between the initial T-vector and the current T-vector.

TC-VM (mV) is the T vector magnitude change and represents the distance between the initial and current T-vectors.

Selected ones of the relative and absolute parameters describing the course of the ischemia may be chosen for display and plotted in a trend graph. The three most common are the QRS-VD (morphological changes) and ST-VM (st-measurements) and STC-VM (st changes).

Figure 14:
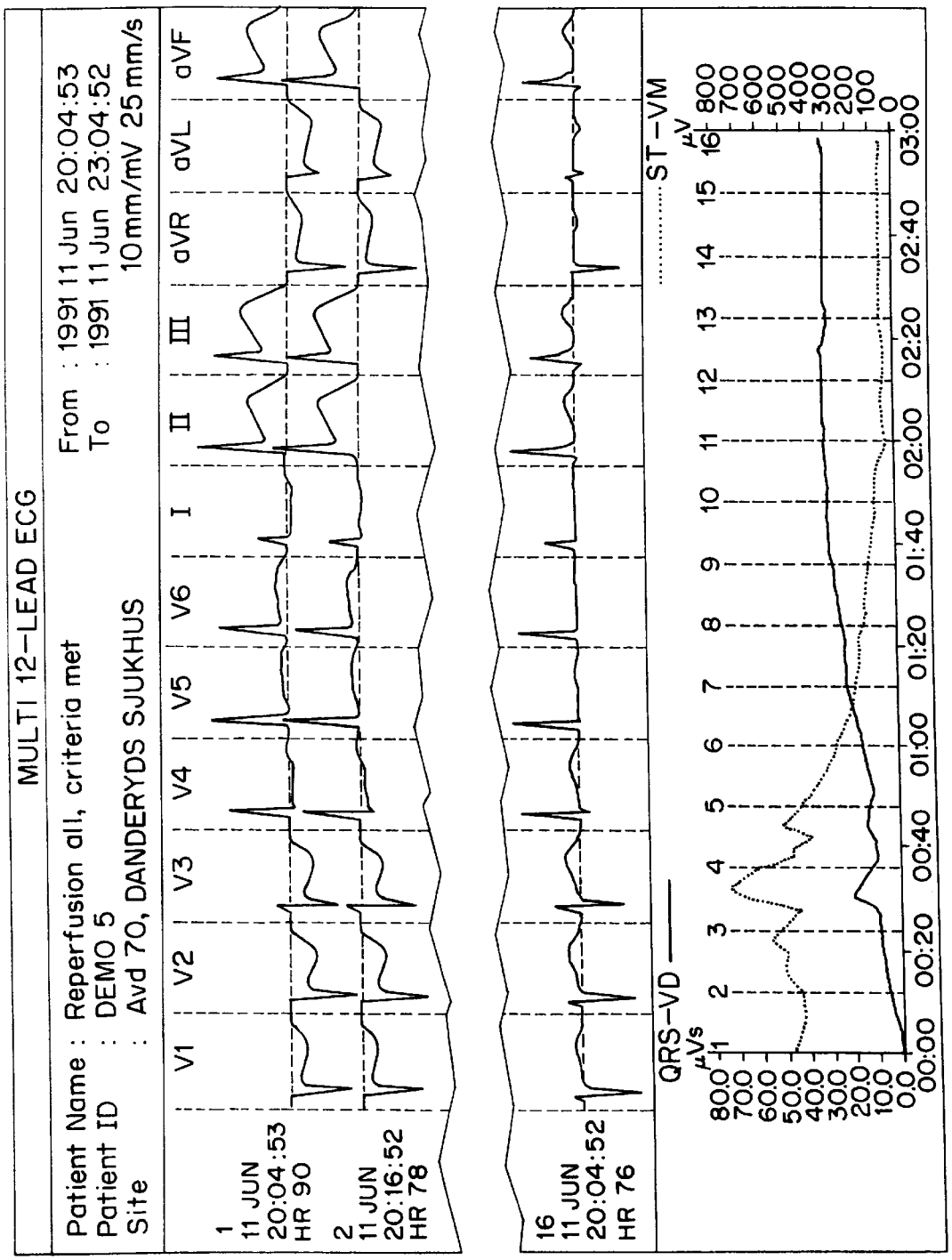
FIG. 14 shows an example of a single page printout, having a plurality of ECG signals printed under each other, produced by the invention.

The averaged ECG that is stored at the end of each time interval contains the values for each of the X, Y, and Z leads. Since the X, Y, and Z contains all information of the ECG, it may also be used to calculate a full 12-lead ECG in real time using a known algorithm. This way, the preferred embodiment may also continuously display a calculated averaged 12-lead ECG for every minute during the entire monitoring period of up to 48 hours in the format of a 12-lead ECG on central workstation 11. Based on the continuously stored X, Y and Z leads, a continuous calculated 12 lead ECG could also be displayed next to a chart with the occurrence of arrhythmias over a selectable range of hours marked as colored bars. The preferred embodiment may also produce a single page printout with a plurality of 12-lead ECG signals printed under each other. See, for example, FIG. 14. The MIDA trends for each patient may be examined in detail one at a time on the workstation display. The trends of all patients may be monitored continuously on the central monitor using the format shown in FIG. 10. The parameter information can be processed using one or more of the processor capabilities available in central workstation 11 and/or bedside monitor 13. Analysis of the trends, as will be described below, can also be performed at central workstation 11 and/or bedside monitor 13, with the results of analysis being displayed at monitor 10 and/or monitor 13.

Depending on the amount of memory provided, the MIDA recording may last, for example, only approximately 48 hours at one-minute intervals. After that, the memory is full and the recording is automatically stopped. Below is an exemplary chart comparing MIDA time intervals to maximum length of the recording.

| MIDA Time Interval | Maximum Length of Recording |
| --- | --- |
| 10 seconds | 8 hours |
| 15 seconds | 12 hours |
| 30 seconds | 24 hours |
| 1 minute | 48 hours (two days) |
| 2 minutes | 96 hours (four days) |
| 4 minutes | 192 hours (eight days) |

The arrhythmia full disclosure works differently, always keeping the most recent 24 hours in memory.

The setup menu contains a MIDA Relearn key to control the MIDA method. When the MIDA Relearn key is selected, the workstation display shows the latest ECG signals acquired with beat labels (beat labels are updated approximately 30 seconds). Every detected QRS complex is labeled with an "M" if it is recognized as a MIDA type of beat (matches the MIDA template). The present MIDA Reference Complex is displayed to the left of the 20 waveforms as scaler X, Y and Z leads. This is the actual, initial, averaged beat to which all subsequent beats will be compared when calculating the relative trend parameters.

The system provides a Restart MIDA key in the MIDA setup display for beginning the process over again. If the Restart MIDA key is selected, a warning message is displayed with options to cancel (No/Cancel) or proceed (Yes). Then a message "Selecting MIDA template, please wait for 20 seconds" is displayed with an option to cancel.

If the process is not cancelled, a suggested new template is displayed in a square for consideration by the user along with three keys for selection. If the Yes key is selected, the entire previous MIDA recording is erased, the suggested template is accepted and the method is restarted. The display is reset, but with no MIDA Reference Complex displayed, since no new Reference Complex has yet been formed. If the No key is selected, the template selection procedure is restarted and a message asking the user to wait for 20 seconds is displayed.

The MIDA system also includes a "MIDA Relearn" feature, the steps of which are identical to the Restart MIDA command described above except that the previously recorded and stored data is not erased.

This feature is appropriate when the MIDA analysis is no longer capable of tracking the ECG. MIDA relearn will find a new template for including ECG complexes in the analysis. (ECG changes always refer to the initial, reference ECG.)

The system also permits the user to review the MIDA Signal Status 107 included in the display, shown in FIG. 10, for each patient. The signal status for all patients is displayed in a Signal Status table when the Signal Status key in FIG. 9 is selected. Below is a list of different possible MIDA signal status messages in order of priority. The line with message of highest priority is indicated with a red background.

1) No MIDA Recording possible with current patient cable. An 8-lead cable is needed for the MIDA recording. If a 5-lead cable is in use, this message is shown.
2) MIDA Recording Ended. The MIDA Recording may last for a maximum of 48 hours with one-minute intervals. When the memory is full, the recording is automatically stopped and this message is shown.
3) No MIDA Recording due to Spikes on signal. A signal spike is a very short disturbance of considerable signal strength. The origin of the disturbance may be pacemaker spikes, bad lead wires or electromagnetic radiation from other equipment. The system will automatically turn the spike filter off if the patient has got a pacemaker, as indicated in the Patient Info function.
4) No MIDA Recording due to Noisy Signal. Noise may be caused by many reasons. Bad patient electrode connection may be one reason. Line disturbances from other equipment close to the patient cable may be another.
5) No MIDA Recording due to Baseline Drift. If the baseline drift is too big, this may distort the ECG. To prevent this, the MIDA Recording is halted. (Baseline drift is a variation in the offset voltage)
6) No MIDA Recording due to lead fail. One of the ECG leads is not working properly.
7) No MIDA Recording due to no reference type of beats. This message is active if the minimum number of reference type of beats was not received during the previous MIDA interval.

Figure 15:
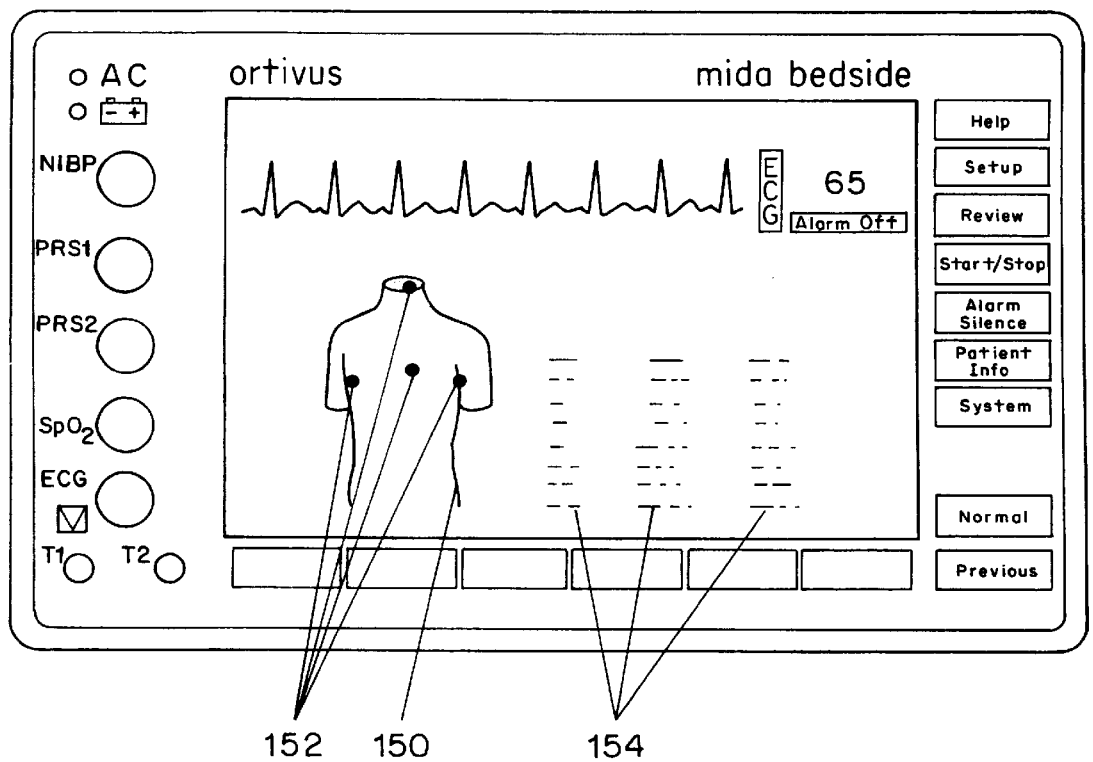
FIG. 15 shows a the display of a patient's torso on a display device along with electrode status indicator lights and annunciator means.

In another embodiment of the invention shown in FIG. 15, a graphical depiction of at least part of the patient 150 is provided and status signal lights 152 corresponding to each electrode connected to the patient are disposed on the graphical depiction 150. Further, status annunciator means 154 corresponding to each electrode, which may provide alphanumeric output, may be provided for indicating the status of each electrode. The status of each electrode (whether a MIDA test is being done or not) may be one of conditions 3, 4, and 5 discussed above, for example. In addition, the status annunciator means may indicate that an electrode has failed, is not properly connected to the body, or in fact has even fallen off, which conditions are manifested as a high electrode impedance. Further, the impedance itself may be displayed by the status annunciator means. The status signal lights may blink to call attention to the status annunciator means and to pinpoint to which electrode(s) the information conveyed by the status annunciator means are directed. The display may be any suitable means, such as a CRT (color or monochrome), active LCD (TFT), passive LCD (SDN), plasma, electroluminescent (EL), or ferro LCD, for example. The display may also be produced by a projector.

The system may also utilize a back position sensor. Since the heart is relatively mobile in the chest, it is only natural that it changes position within the chest when the patient changes position in the bed, e.g. from lying on the back to lying on the side. Since the electrodes record the electrical activity on the surface of the chest, the movement results in a change in the ECG. The influence of this change affects each of the MIDA parameters differently. Since ST-VM measures the strength of the ST deviation, regardless of direction, it is less sensitive than other "ordinary" ST measurements. The parameter QRS-VD is, however, very sensitive to these changes. A back position sensor makes it possible to tell if a change in the trend was caused by change of body position or not.

The Back Position Sensor connects to the junction block of the 8-lead ECG cable. The information from the back position sensor is recorded and displayed on a separate line below the trend graph. This line may have three colors indicating the following states:

| Color | State |
|---|---|
| Green | On Back |
| Yellow | Not On Back |
| Grey | No Trend available |

The MIDA trend may be displayed on the central monitor as described previously. The Trend key also arranges for the picture to be displayed on the display of the workstation for review.

Keys appear to the left allowing the user to select what trend will be displayed. These keys may be labeled MIDA and HR/PVC. Up to four different trend curves may be displayed in the trend graph. To be able to tell the curves apart, they are displayed in different colors. The name of each trend curve is also written over the graph in the same color as the curve itself.

The system provides a cursor, controlled by the mouse, in order to, for example, mark points of special interest. (If points of special interest are marked in the trend curve, they may be of assistance when examining the corresponding 12-lead ECGs.) By pointing and clicking in the trend, the cursor is moved to the desired time. Alternatively, the cursor may be moved step by step by pressing the right and left arrows under Cursor labels on the bottom of the display of the trend graph. The system displays time of the trend graph corresponding to the position of the cursor on the top of the graph, both as time of day and time since admission. The system also displays the exact values of the parameters to the left and to the right of the time.

Points are marked by placing the trend cursor at the desired time and selecting the check key which is displayed between the arrows under the Mark label to the right under the graph. When the trend cursor is placed on a marked time, the system turns the check key to yellow.

The user can jump directly between separately marked times by selecting the right and left arrows under the Mark label. The system unmarks a time whenever the user presses the check key again.

The system also permits the user to change the parameters in the trend graph. (Users normally select the QRS-VD and ST-VM6 parameters for display in the trend graph. The MIDA analysis includes thirty parameters that are continuously calculated and stored.) The MIDA trend display contains keys under the Trend parameter label which select the axis to be affected (Le1=Left one, Le2=Left two, etc.). A table of different parameters will then be displayed in response to the selection of an axis. The user then selects the key of the desired new parameter to be trended. A Return key is selected to return to the graph.

The system further permits adjustment of the timescale of the trends to include the most interesting parts of the trends. Zoom keys are displayed, which, when selected, make it possible to enlarge certain parts of the trend curves. The system is set up so that "zooming" is centered around the cursor, which can be placed in the middle of the interesting part of the trend curves by pointing and clicking with the mouse. Every time the left "−" zoom button is pressed, the curves around the cursor are expanded. The right "−" zoom button has the reverse effect; it goes back and shows bigger portions of the curves.

The system also provides a Scale key, which when selected displays additional keys which enables the user to adjust the size of the displayed graph. The height of the trend graph(s) may be increased or decreased by selecting arrows under the Max label to the left and to the right of the graph. The baseline offset may be adjusted by selecting the arrows under the Offset label.

After the scales have been changed, they may be reset to default at any time by pressing the Normal key.

Again, a Return key must be selected to return to the graph. The system further allows the time to be changed with a key displayed on the bottom right hand side. Clock time is the time of day (8:30 means eight thirty in the morning) while Relative time is time since admission (8:30 means that the patient has been monitored for eight and a half hours).

It is also a particular advantage of the system employing the method that a number of settings controlling the MIDA analysis may be adjusted to customize the analysis. The MIDA setup is available through the MIDA Setup key.

The different settings are described below, one by one. Each group of settings may be reset to default values individually by pressing the Normal key next to each group.

The MIDA interval is the time interval within which the MIDA analysis will produce new values. During each interval, all acquired ECGs of sufficient signal quality that match the initial reference ECG will be averaged to form an ECG with improved signal quality. At the end of the interval, the averaged ECG is used when calculating the MIDA parameters. The averaged ECG and the 5 parameters values of every such interval is stored in the Acquisition Module for approximately 3000 intervals.

Short intervals (less than 1 minute) have the advantages of fast response to rapid ECG changes, but they also have more noise and result in a shorter total recording time. Long intervals (more than 1 minute) have less noise and result in a longer recording time but they also respond slowly to rapid ECG changes. Generally, one minute intervals are recommended for CCU monitoring (infarction, unstable angina, etc.) and 15 second intervals are recommended for PTCA use. The default setting is preferably 1 minute.

To form an averaged ECG at the end of the intervals previously described, a minimum number of beats must have been included in the average. Too low a limit may result in poor signal quality. Too high a limit may result in difficulties reaching the limit with no calculated parameter values as a result. Naturally, the minimum number of beats required is dependent on the interval length. Recommended setting:

| MIDA interval | Minimum number of beats |
|---|---|
| 10 seconds | 1 beat |
| 15 seconds | 1 beat |
| 30 seconds | 2 beats |
| 1 minute | 2 beats (factory setting) |
| 2 minutes | 10 beats |
| 4 minutes | 10 beats |

If the signal quality of the acquired ECG is too poor, the ECG will not be used for MIDA analysis. This is to avoid false results—artifacts. Each ECG signal has to pass the following tests to be included in the MIDA analysis.

A signal spike is a very short disturbance of considerable signal strength. The origin of the disturbance may be electromagnetic radiation from other equipment, bad lead wires or pacemakers. The spike test may be turned on or off. When spikes are detected, the MIDA analysis is halted unless the patient has a pacemaker.

Noise may be caused by many reasons. Bad patient electrode connection may be one reason. Line disturbances from other equipment close to the patient cable may be another. The noise threshold may be set to 5, 10, 20, 50 or 100 micV or may be turned off. When excessive noise is detected, the MIDA analysis is halted. The default setting is 50 $\mu$V.

If the baseline variation is too big, this may distort the ECG. The baseline threshold may be set to 25, 50, 100, 200 or 400 micV/second or be turned off. When baseline variation is detected, the MIDA analysis is halted. The preferred default setting is 100 micV/sec.

The default settings may be selected by the user in a table of default settings which is opened by selecting the System key and entering an access code. The table includes a Save key and a Cancel key which, when selected, respectively set the default settings or close the menu with no alterations to the default settings.

Another Embodiment

Another embodiment of the invention may be used as a complement to a conventional monitoring system for enhanced monitoring and documentation of the ECG in terms of ischemia, infarction and arrhythmia.

This embodiment also has the advantages of ischemia monitoring with parameters reflecting the ECG changes in clear trend graphs, averaged 12-lead ECG acquisition, storage and display, arrhythmia detection, 24-hour full disclosure arrhythmia of all monitored patients, and 24-hour continuous 12-lead ECG stored for all monitored patients.

However, this embodiment does not contain a monitoring system with waveforms and arrhythmia alarms. Rather, it is a system for only monitoring ischemia and the course of various heart diseases. Waveforms and alarms are controlled and monitored using the conventional monitoring system.

It consists of the elements shown in FIG. 7, except that instead of a bedside monitor, it has an Acquisition Module for each patient, connected via Ethernet to a central Server. The server displays and stores data from all connected Acquisition Modules. It is a supplement to a conventional monitoring system adding the functionality described above.

The Acquisition Module works in parallel with the patient monitor of the conventional monitoring system. The ECG signal from the patient is fed into both the Acquisition Module as well as the patient monitor. The parallel connection is achieved with an adapter cable between the acquisition module and the patient monitor.

The Acquisition Module acquires the signal, converts it from analog to digital and performs ischemia and arrhythmia analysis. The Acquisition Module communicates with the central Server via an Ethernet connection on the back. It also includes a serial port for connection to other devices, such as the Hewlett Packard VueLink interface module.

FIG. 12 shows a face of an Acquisition Module. Element 121 is an ECG input for use with either 8-lead or 5-lead patient cables. Element 122 is a Signal out for connection to the ECG input of the conventional monitor. Element 123 is a graphic depiction of the patient, which in this case incudes only the torso. More or less parts of the patient may be included in the graphic depiction of the patient, for example, the limbs. A number LEDs or other light producing means are placed behind the graphic depiction of the patient, each at positions corresponding to the electrodes on the patient's body. Each electrode may be indicated individually with a twinkling yellow light if the signal quality is poor or with a steady yellow light if the lead fails. When the signal quality is all right, all electrode indicators are off. Alternatively, the electrodes may blink at different rates or display different colors depending upon the conditions of the electrodes discussed with reference to the second embodiment. The graphic depiction of the patient may be silk screened, wet painted, powder coated, multi-color molded plastic, or overlay film, for example. Element 124 is a MIDA status indicator with a green and yellow indicator. The green indicator is on when MIDA analysis is running. If the MIDA analysis is not running for anyone of various reasons, the yellow indicator is on. Element 125 is a back position indicator. A back position sensor is a position sensitive device that may be used to record if the patient is lying on his back or not. This information may be useful when examining the most sensitive parameters such as QRS-VD of the MIDA analysis. When such a sensor is used, the back position indicator is green only when the patient is lying on his back. Element 126 is an event Mark key. When this key is pressed, an event mark is recorded by the system. Element 127 is a Pause key. The recording may be paused and resumed with this key. When paused, recording and analysis are temporarily halted. This is indicated with a yellow light behind the pause symbol. Element 128 is a Discharge Patient key. When this key is pressed, the current recording is terminated and the MIDA module is ready to start a new. Element 129 is a Main Power operation indicator. A green light indicates that the module is on, running on main power. Element 130 is a Battery Power operations indicator. A yellow light indicates (a warning) that the module is on, running on the internal battery for very limited time. Element 120 is an On/Off Switch. The module is turned on by pressing the switch. The module is turned off by pressing the switch again.

The patient input of the MIDA Acquisition Module is of Type CF, it is defibrillation proof (it may remain connected to the patient during defibrillation), and the patient connector on the front is marked with the appropriate heart symbol.

The patient input of the MIDA Acquisition Module is designed to limit the current through the patient to a few microAmperes and to comply with the requirements for low leakage currents when connected to a conventional Monitoring System. If other equipment than the MIDA Acquisition Module is connected to the patient, it should be interconnected with an equipotential grounding cable. On the back of the MIDA Acquisition Module there is an equipotential grounding terminal for this purpose. The following connections are provided on the rear (not shown) of the MIDA Acquisition Module: AC in—to be connected to a grounded electrical AC source of 100–240 V+–10%, 50–60 Hz. Equipotential grounding terminal—used to obtain the same electrical earth reference when additional electrical equipment is used together with the MIDA Acquisition Module. Ethernet—for connection to the Ethernet network. RS-232 Serial communication—for connection to other devices, such as a Hewlett Packard VueLink module.

The Acquisition Module is equipped with an internal battery that is switched in as soon as the AC power is insufficient. The internal battery provides full operation for at least five minutes, when fully charged. When the MIDA Acquisition Module operates on the internal battery, a yellow LED is lit in the lower right corner of the front, under the battery symbol. The internal battery is recharged as soon as the AC power is back and the Module is on. Line power operation is indicated by a green LED in the lower right corner, under the AC symbol.

Workstation 11 also contains a 17" color monitor on which curves and data from one patient at one time may be brought up for examination. The workstation also contains a graphical interface with a mouse, which may be used to control the operation of up to two of the central monitoring units. However, the central monitors are not disturbed at all when the monitoring of one specific patient is controlled or examined at the workstation. All information presented on the workstation at any time may be printed on the laser printer.

A row of keys on the top of the workstation monitor allows selection and direct control of the monitoring of each patient. The keys are marked with an identification tag for each bed (normally 1, 2, 3 and so on). When a patient has been selected, the operator may control admission/discharge, alarm settings, waveforms monitored, and much more in a straightforward and easy manner using the graphical interface. A monitoring session may also be examined in detail in terms of ischemia, 12-lead ECGs and full disclosure arrhythmias.

When the ischemia trends are examined on the workstation, any one of 30 different calculated parameters may be examined over time. Interesting events may then be expanded on the screen and exact values corresponding to the events will be shown. Short events can be expanded to display a couple of minutes on the display even if the entire trend covers several days of monitoring.

The system in the preferred embodiment of the invention reduces the need for additional 12-lead ECGs. Minute-by-minute, derived 12-lead ECGs are automatically acquired and stored in the system. Several 12-lead ECGs may be superimposed from different times in order to plot gradual changes. By pointing out interesting ischemic events in the ischemia graphs, the corresponding 12-lead ECGs may be displayed, superimposed or printed on the laser printer, if desired. Thus the morphologic nature of the ischemic changes may be examined in real time, i.e., during thrombolytic therapy or unstable angina.

Workstation 11 also contains a complete 24-hour full disclosure arrhythmia review function. The arrhythmia graph is presented on the lower half of the workstation display, with the arrhythmias plotted as colored dots or lines depending on the duration of the arrhythmias. The corresponding ECG is displayed on the upper half of the display. Every single heartbeat during the previous 24 hours can be displayed for each monitored patient by pointing out either the arrhythmia of interest or the desired time of day.

The system also contains a data storage unit for storing all data from the monitoring session for future examination. A stored recording may be examined on the workstation in exactly the same way as currently monitored patients.

The preferred embodiment of the invention described above uses a complete networking system for a number of patients to perform the following analysis and monitoring. However, this method of analysis and monitoring may be technically implemented using different hardware, system architecture or a special program code in a different program coding. The method may, for example, be used in a standalone system for a single patient.

Ambulatory and Telemetry Application

The method may also be used in an ambulatory application. In such an application, ECG signals are recorded over a long period of time by a recording device worn or carried by the patient. The recorded signals are later retrieved for printout and analysis. The signals may then be analyzed according to the method described here below.

In a telemetry application, the patient carries a small transmitter which transmits the ECG signals to a receiver where the signals are displayed in real time. The ECG signals received by the telemetry system are then analyzed according to the following method.

Portable Telemedicine Device

Figure 27:
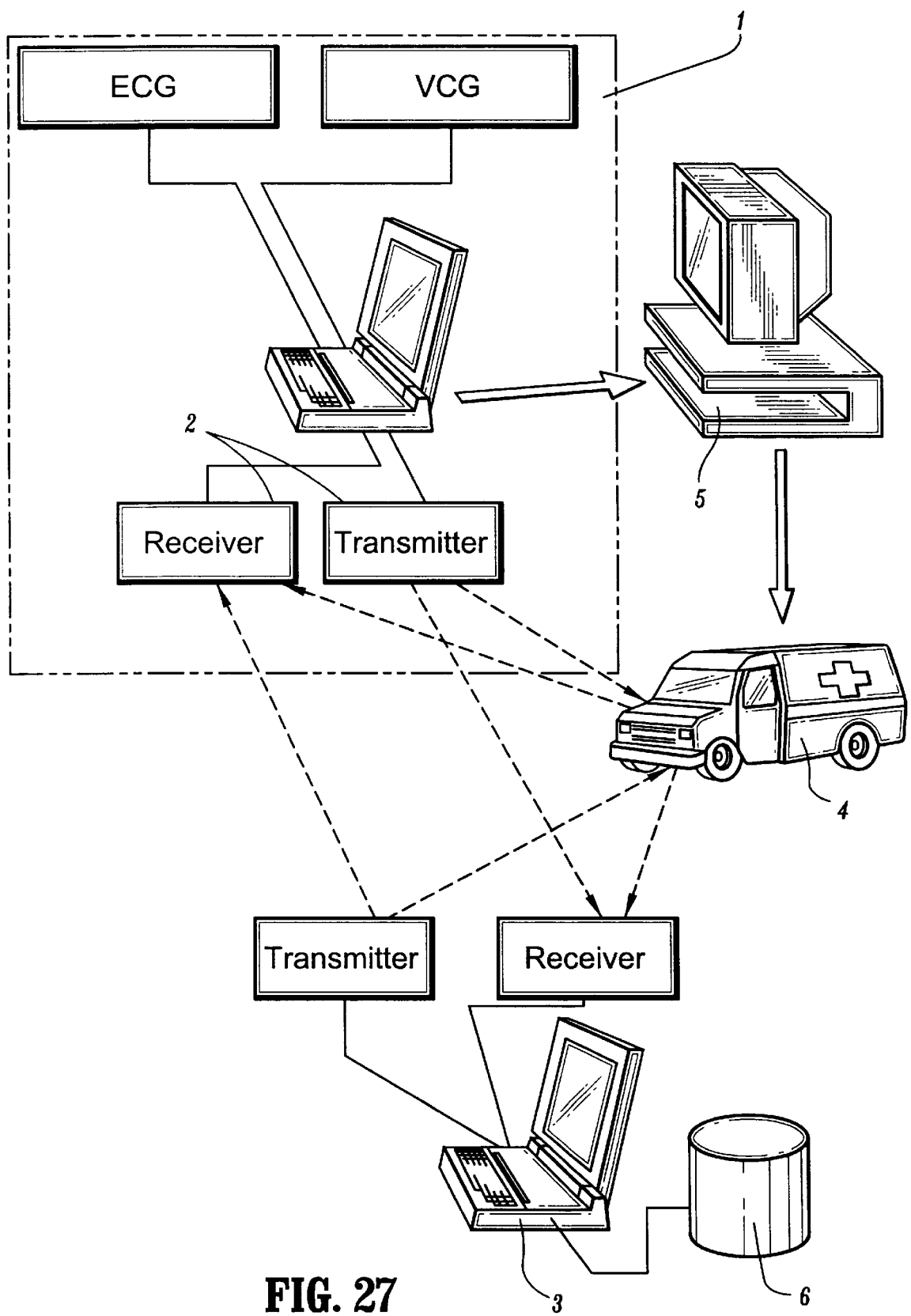
FIG. 27 is a schematic view of a system comprising a portable telemedicine device in accordance with the invention.

As shown in FIG. 27, the invention also comprises a portable telemedicine device 1 including integrated measuring equipment, such as ECG and VCG, input means for connecting external measuring sensors, a display for displaying the measurement data and the like, entry means for entry of other measurement data, patient's name, observations and so on, and communication equipment 2. The portable telemedicine device in accordance with this embodiment of the invention preferably is an easily manageable, integrated unit, illustrated in FIG. 28. Preferably, this unit also is provided with a rechargeable battery unit, which adds to the ambulatory nature of the device.

Again referring to FIG. 27, the communication equipment 2 may be arranged to transmit digital data via a mobile telephone network, such as GSM or the like, via the MOBITEX network or by any other suitable means. Thus, the telemedicine device may communicate directly with one or several central units 3 or via one or several intermediate stations, such as for instance an ambulance 4. Additionally, the communication may be established via option communication means, such as GSM and MOBITEX, as selected in accordance with the conditions in each individual case.

Preferably, the central units are data-processing devices capable of receiving information data and presenting the latter in real time, and also capable of emitting information data to portable units. The central unit preferably also is capable of communicating with other systems, of storing information data, and of later displaying such stored information data.

The portable telemedicine device further is advantageously equipped with a connecting interface for allowing convenient docking thereof to stationary equipment 5, e.g. onboard an ambulance or inside a hospital. The docking interface may be designed to shift its mode of communication at the instance of docking, to allow transmission via another telecommunication network or via cables coupled to the stationary equipment. In addition, the docking may involve connection to network voltage, battery chargers, external entry means (such as keyboards), external displays, and so on. Further, the portable telemedicine device could be adapted for communication via IR transmission using equipment known in the field, such as PDA equipment (Personal Digital Assistants) and the like.

The device may also be adapted for automatic selection of a telecommunication network in response to current reception conditions, in order to offer the best possible transmission performance. Such adaption may depend on the type of information data to be transmitted and on the manner of the transmission. In this way it becomes possible to use different networks for transmission, for example, of large data volumes that must be transmitted to a receiver within a brief space of time, and of short messages that are to be transmitted to several receivers. For instance, the device may utilize networks of such a different nature as the circuit-switched GSM network and the packet-switched MOBITEX. However, to achieve this versatility feature, adaptations are required in the form of different software as well as different hardware. To make it possible to use such a comparatively slow transmission system as the MOBITEX, selection and pre-processing of data are required as is also compressing of the data.

When the portable telemedicine equipment is intended for use by ambulance staff or other ambulance personnel, it is advantageously brought along when the ambulance staff is called to the patient. The sensors associated with ECG, VCG and the like are connected, and a first diagnosis then may be made. In some cases it may, however, be more appropriate to defer connection of the equipment until the patient is onboard the ambulance.

The display preferably is divided into different fields, showing for example:

Information on the patient's name, patient ID number, time, and the like;

Monitoring information received from the measuring equipment, such as continuous ECG monitoring, blood pressure monitoring, continuous curves indicating the variations in the oxygenation of the blood, and the like;

ECG reports, "cuttings" from real-time curve graphs, tendencies, patient case record files, other information, recently received messages, and the like;

Up-to-date values of collected measurement data and set alarm limits;

Menu of currently selectable commands;

Status of communication equipment, such as available connected receivers and the band width of the communication channel;

Messages received and emitted, inclusive of facilities for browsing through old messages;

Setting options, e.g. different communication networks, reception and transmission via ambulance or not, different areas of application, choice of external equipment to be connected, and the like.

In addition, the menu system could advantageously can be designed to comprise several levels, including one main menu and one or several levels including sub-menus.

Following connection of the equipment, information data is entered, either automatically via the measuring instruments or manually by the patient-attending staff. Some information data, such as that relating to certain measurement results, annotations entered into patient case record files, patient information and the like then are transmitted automatically to the predetermined receivers to which the device is connected, whereas other information data is forwarded only as ordered by the attending staff. A transmission list determines which receivers are to be used in each individual case, from which list one or several central units may be preselected. Preferably, the list may be altered in the process of use.

The information to be transmitted may be assigned different priorities, the information data most essential for correct diagnosis and for the implementation of correct treatment being given a higher priority and being transmitted prior to information data of less importance. This feature is particularly advantageous for instance when the capacity of the communication network is such that the latter is slow in transmitting the information and when it may not even be possible to transmit all information. The priority feature may be implemented manually, or, which in most cases is the preferred alternative, automatically with the aid of software, or else a combination of the two varieties is possible. The medical usefulness should, at all times, govern the priority.

In addition, the portable telemedicine equipment is supplied with information data from the central unit, on the one hand in the form of messages from e.g. specialist physicians or the co-ordinating control group and on the other in the form of data from the patient's case record file and the like, data which already is stored in databases 6 in the central unit.

In addition to its use in showing measurement results, the portable telemedicine device in accordance with the invention can also be used for filling in certain forms, such as patient's case record files and the like, in addition to which it offers facilities for communication with a central unit (or several central units) via the telecommunication network. The central unit could be positioned e.g. in the closest large hospital where the received information data could be examined by specialist physicians of the relevant medical discipline and a correct decision be taken rapidly, both with respect to the treatment to be implemented right away and to the planning and the preparations for the continued treatment. In other words, owing to the communication facility, measurement results and other entered information data are transmitted in full or in part from the portable telemedicine equipment to the central unit, and the information data, which may include treatment counselling, queries relating to the diagnosis, information regarding where to transport the patient, and the like, are transmitted from the central unit to the portable unit. In addition, all dialogue preferably should be stored in the portable unit and/or the central unit.

The various components of the device are, as stated above, preferably integrated in an easily manageable unit, thus making it simple to handle, and versatile and easy to transport and to connect.

Additional equipment may be included as parts of the device or be connectable thereto, such as printers, cameras, microphones, and loud-speakers depending on need, communication channel capacity and the like.

Figure 28:
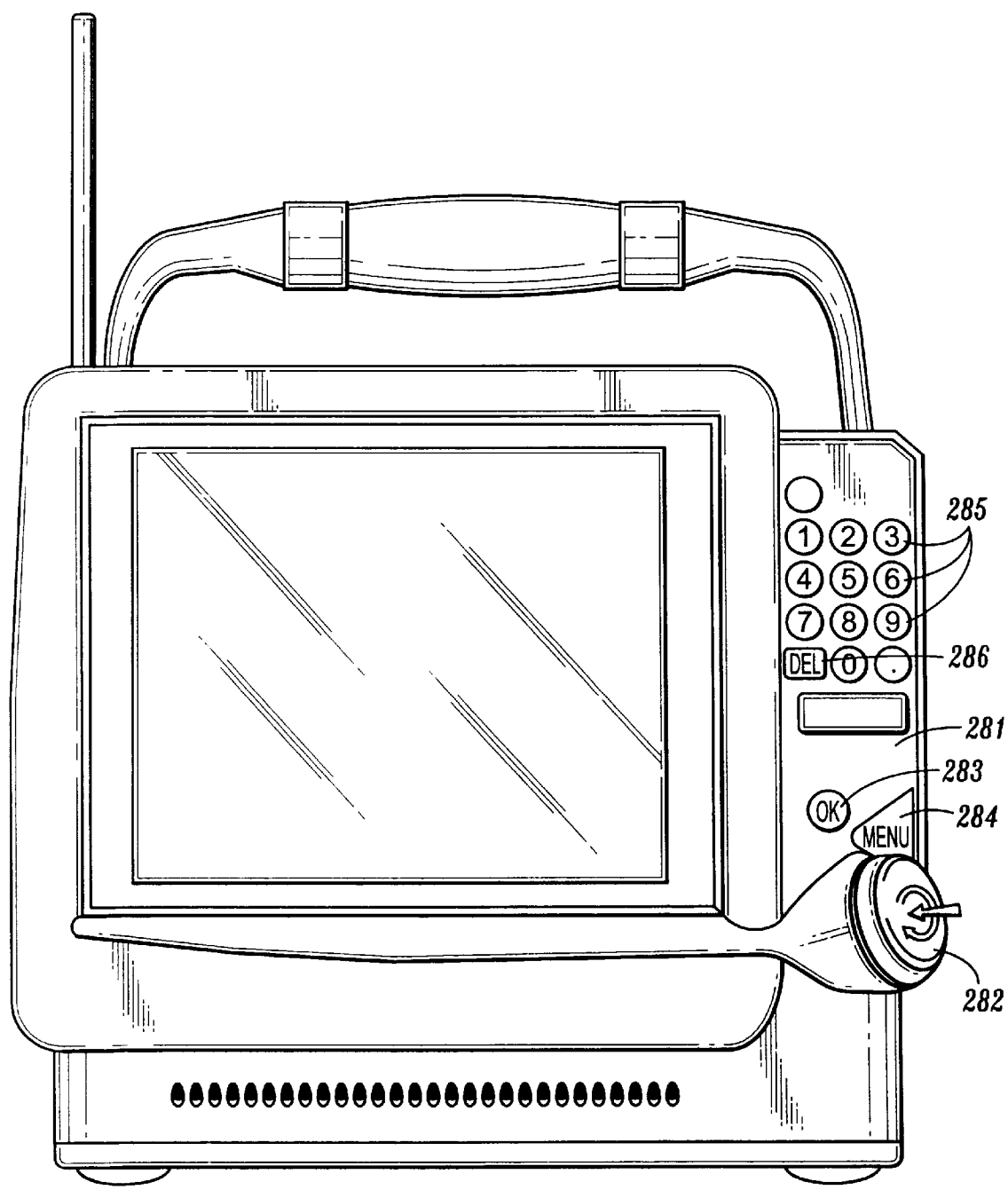
FIG. 28 is a view of a preferred embodiment of the portable telemedicine device of FIG. 27.

As appears from FIG. 28, the entry means comprises a bottom plate 281 formed with an entry means including a rotatable and depressible actuating member 282 in the form of a ball or a wheel, and of additional entry buttons 283 and 284. The actuating member affects a cursor on the display screen in such a manner that the cursor moves in response to actuation of the actuating member. The cursor is only moveable backwards and forwards between points in a predetermined order. For instance, the cursor movement could be upwards and downwards in a vertically arranged menu, jumping between a number of different windows on the screen or the like. Upon depression of the actuating member 282 the object highlighted at that moment by the cursor is activated (i.e. the function identical to that of the "ENTER"-key on an ordinary keyboard). In this situation, either the indicated function is performed, involving for instance entering an object in a form, or else a sub-menu appears, whereupon the procedure is repeated.

In this manner it becomes possible to enter text or numbers, in that by turning the actuating member the operator may proceed through the entire alphabet or the numbers and by depressing the member 282 indicate the letters or numbers he or she wants to enter.

Of the extra entry buttons of the entry means, one button 283 is for verifying incoming messages or alarms and one button 284 for moving to a superior menu level. In addition to these two buttons, the entry means may be supplemented with numeric keys 285 representing digits 0–9, in order to render the data input more efficient, should the entry items comprise several measurement values in digital form. In addition, the entry means preferably comprises a delete button 286 to erase entered values.

An entry means in accordance with the invention occupies but a fraction of the space required by a conventional keyboard, in addition to which it can advantageously be placed vertically, a position most unsuitable for conventional keyboards. For instance, an LCD display and an associated juxtaposed entry means in accordance with the invention, easily may be placed in positions where conventional terminals cannot be used. In addition, the entry of input data easily may be effected using one hand only.

Figure 29:
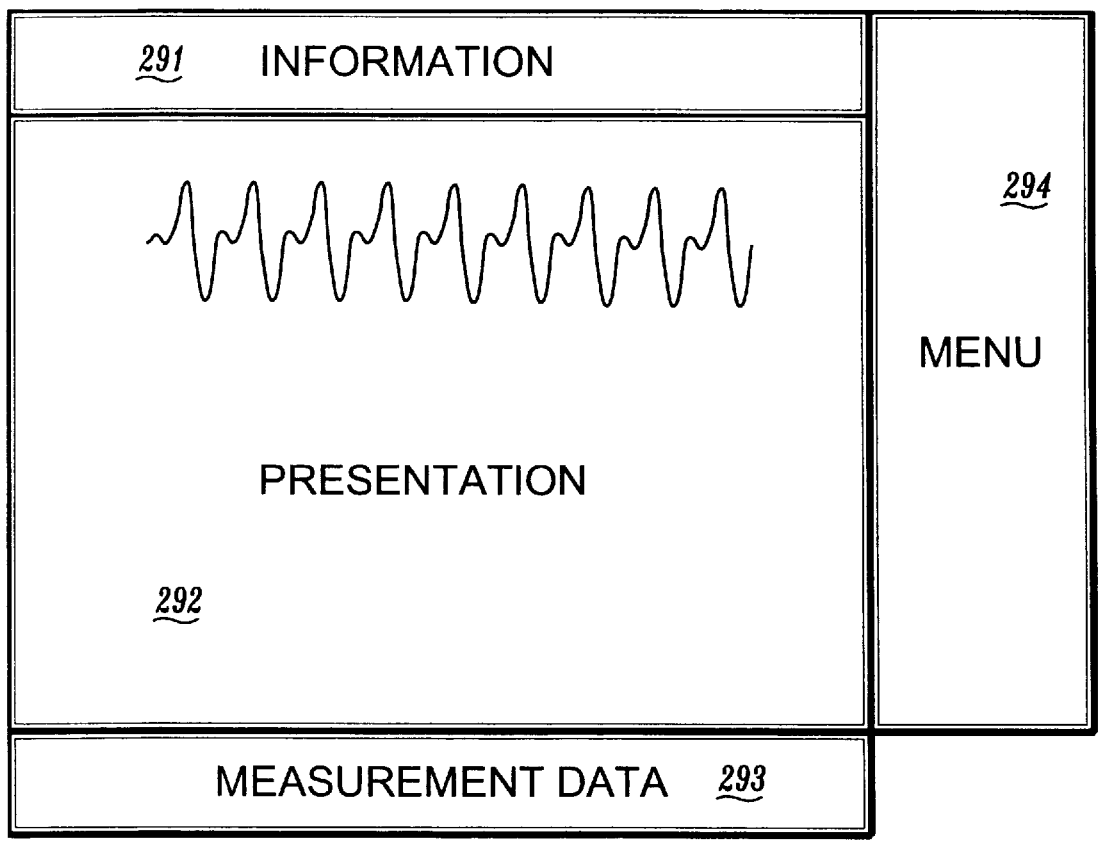
FIG. 29 illustrates a first example of a display layout intended for use together with the device of FIG. 28.

When the entry means is used as described above, the display preferably is divided into several fields, such as shown for example in FIG. 29. One example of a display layout is illustrated that may be used by medical services personnel and that comprises one field 291 containing information on patient's name, identity number, information on the status of the communication and similar comprehensive information, a second field 292 containing a presentation, for instance, in the form of curve graphs, representing incoming measurement values and the like (e.g. from ECG), a third field 293 containing measurement data derived from other (or the same) measurement instruments and alarm limits, and a fourth field 294 containing a menu of selectable options. As the actuating member is rotated, different menu options will be highlighted in a predetermined order. This predetermined order could be e.g. from the top towards the bottom, or inversely, depending on the direction in which the operator rotates the actuating member. The highlighted option is activated upon depression of the actuating member, causing either the activation of a function or the appearance of a new sub-menu.

Figure 30:
FIG. 30 illustrates a second example of a display layout intended for use together with the device of FIG. 28.

FIG. 30 illustrates one example of the configuration of a display upon activation of a "case record file" function for entering information data into the patient's case record file. Under this option heading, a sub-menu appears. In this case, the sub-menu comprises four different case record fields and three additional menu options. To enter data, the operator/attendant turns the actuating member 282, causing the first case record field to be highlighted, whereupon he or she depresses the actuating member to activate the highlighted field. In this field, there are two alternative choices: input of personal code number and input of personal name. As the personal code number is entered, this option is highlighted in the same manner as mentioned above, whereupon one digit at a time is entered. This could be achieved by means of a line of numbers which appears on the display and from which desired numbers are chosen through rotation and depression of the actuating member. Alternatively, the highlighted number is increased or decreased by means of rotation of the actuating member, followed by depression of the member, the corresponding number thus being chosen and the cursor made to proceed to the next position, and the procedure is repeated.

In order to return to the immediately superior menu the latter either could be permanently available as a last selectable menu option or else retrievable by use of the particular return button. An entered digit could be cancelled/deleted with the aid of the button provided for this purpose.

Entry of letters is effected in the same manner as entry of numbers, and numbers as well as letters as also other signs may be selectable in all positions.

In addition, the entry procedure in many cases may be simplified, when only a restricted amount of entry options exists or occurs frequently. In such cases, the data entry may be effected via a menu comprising predefined options, such as shown for example in the fourth, lowest case record field in FIG. 30. In this field, the diagnosis, such as "angina pectoris", may be entered by advancing the cursor through rotation of the actuating member until the cursor reaches the relevant option, and by subsequently marking the latter.

Several modifications of the entry means in accordance with the invention are conceivable. For instance, the entry means need not comprise supplementary entry buttons but the rotatable and depressible actuating member may suffice. In addition, the actuating member optionally may be divided into two separate means, one of which is rotatable and the other depressible. Other measurement equipment may be coupled to the device. The device could be used in other applications involving services and activities related to nursing and attending of individuals, such as home-help services.

Trend Analysis

The gathered trend data may be interpreted and analyzed in several different ways. For example, according to one embodiment, episode analysis is performed on the data. According to another embodiment, recovery analysis is performed.

ECG trend parameters from stored or currently monitored patients are displayed and analyzed. The analysis can be customized by changing the values of variables in a set of analyzing variables as will be discussed below for each of the types of analysis.

Episode Analysis

Episode analysis can be used to calculate and present indexes on ECG trend parameters including important measurements such as, for example number of episodes, length of an episode, area of an episode and extreme or maximum value of an episode.

Figure 31:
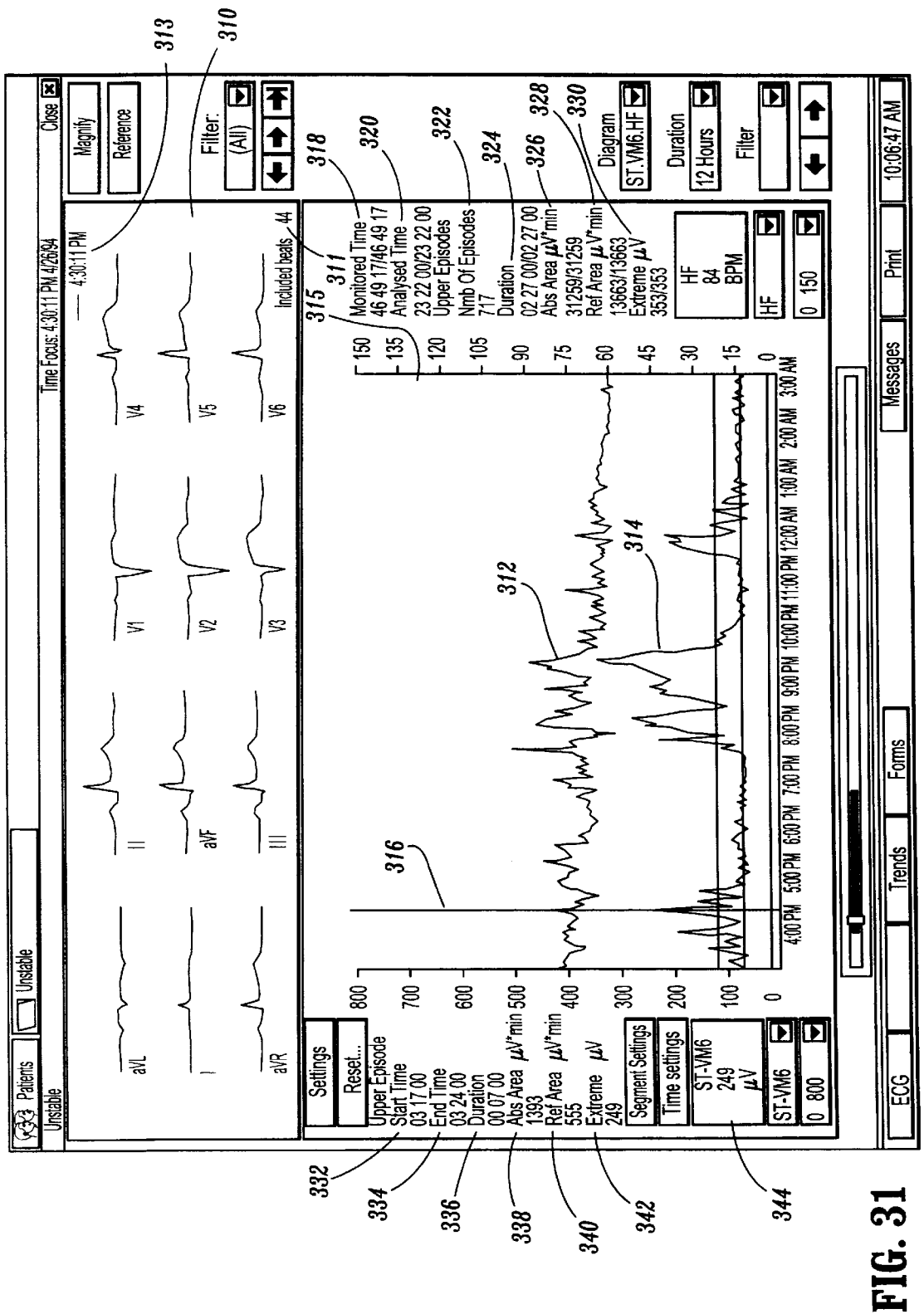
FIG. 31 illustrates another example of a display showing analyzed results.

As shown in FIG. 31, gathered data is displayed in an easy to read and comprehend format. The display includes trend curves and the averaged ECG from which the trend parameters at the time pointed out are calculated. The indexes calculated from the trend analysis are also displayed. The 12 lead averaged ECG signals are displayed in an upper window 310. The number of beats 311 included in the averaged ECG signals is displayed in window 310, along with the time 313. In window 315, first and second trend curves 312, 314, are displayed.

Episode analysis can be used to detect and evaluate the number of episodes in a trend. Analysis of the trend curves can be customized, by changing variables used in algorithms for detecting episodes and calculating episode data. An episode is defined as a number of trend data either being higher than an upper threshold or lower than a lower threshold. The variables that affect the detection of episodes are a) minimum number of trend values (time) crossing threshold to qualify for an episode; b) maximum time allowed between two adjacent trend values within the same episode; c) minimum time allowed between two adjacent episodes; and d) the distance between the baseline and the thresholds.

Default values are set for each variable in the event for which values are not input by the user. The default values include minimum number of trend values crossing threshold to qualify for an episode=120 seconds. This equates to at least two trend values if a 60 second averaging period exists. The minimum time allowed between two adjacent episodes has a default value of 80 seconds. That is, if less than 80 seconds exists between two episodes, they are merged into one episode. The maximum time allowed between two adjacent episodes has a default value of 100 seconds. If more than 100 seconds exits between two adjacent trend values, it is determined that they can not be in the same episode.

Default values for parameter thresholds are $-50\,\mu V$ lower threshold and $50\,\mu V$ upper threshold for ST-VM20, ST-VM60, STC-VM20, STC-VM60, ST-X60, ST-Y60 and ST-Z60. Default threshold values are $-15\,\mu V$ and $15\,\mu V$ for QRS-VD. All parameter default threshold values are relative the baseline.

The baseline reflects the value of a parameter when the patient is not ischemic and there are no artifacts on the ECG. The baseline may be manually set by looking for a period where the trend parameter is relatively stable and where the averaged ECG shows a nonischemic complex without artifacts. The baseline is then set to the value of the trend parameters during this period. The baseline may vary over time. Accordingly, a new segment may need to be defined for each period of the new baseline value.

The monitored time 318 is also displayed and reflects the time the patient is hooked up to the system. Gaps in the trend are not excluded from the monitored time. The monitored time 318 for an entire session (MTS) is:

$$MTS=(T_{LT}-T_{FT})* T_{avg} \qquad (4)$$

where $T_{LT}$ is time for last trend value, $T_{FT}$ is time for first trend value and $T_{AVG}$ time for averaging period at the start.

The monitored time 336 for a segment (MS) is:

$$MS=E_T-S_T \qquad (5)$$

where $E_T$ is the end time 334 of the segment and $S_T$ is the start time 332 of the segment, the first segment starting one averaging period before the first trend value.

The analyzed time 320 reflects the time from which there are resulting trend values. That is, analyzed time 320 for the entire session is the sum of the averaging times for all trend values. The analyzed time for a segment is the sum of the averaging times for all trend values within the segment.

For an upper/lower episode to exist, consecutive trend values must be present for at least the time duration "minimum time for episode" above the upper threshold or below the lower threshold. In addition, a time gap between two consecutive trend values above/below the upper/lower threshold must not exceed "maximum gap in trend". If the time between the end of one upper episode to the start of the following upper episode is less than "minimum time between episodes," the two episodes are merged into one episode. Likewise, if the time between the end of one lower episode to the start of the following lower episode is less than "minimum time between episodes," the two episodes are merged into one episode.

The duration of an episode 324 is calculated as:

$$DURATION=T_{LV}-T_{FV}+T_{AVG} \qquad (6)$$

where $T_{LV}$ is the time of the last trend value in the episode, $T_{FV}$ is the time of the first trend value in the episode and $T_{AVG}$ is the averaging time prior to the first trend value in the episode.

The extreme value 330 of the upper/lower episode is the highest/lowest trend value within the episode.

The absolute area of the episode 326 is defined as $$F_{TV} \times T_{AVG} + \Sigma \text{ trend value} \times (\text{time of trend value} - \text{time of previous trend value}) \qquad (7)$$

where $F_{TV}$ is the first trend value, $T_{AVG}$ is the averaging time prior to the first trend value and wherein the sum portion of the equation includes all trend values within the episode except the first one. It should be noted that if a trend value has a sign opposite than the threshold, the value is excluded from the area calculations. For example, this could occur if two episodes are merged because they occur with a time less than the "minimum time between episodes" and during that time interval such a trend value is present. The trend value following the excluded trend value is considered as lasting from the excluded trend value.

The relative area 328 is defined as $$(F_{TV}-T_T) \times T_{AVG} + \Sigma(\text{trend value} - \text{threshold}) \times (\text{time of trend value} - \text{time of previous trend value}) \quad (8)$$

where $F_{TV}$ is the first trend value, $T_T$ is the threshold, $T_{AVG}$ is the averaging time prior to the first trend value and wherein the sum portion of the equation includes all trend values within the episode except the first one. If a trend value is below an upper threshold in an upper episode or above a lower threshold in a lower episode, the value is excluded from area calculations. For example, this could occur if two episodes are merged because they occur with a time less than the "minimum time between episodes" and during that time such a trend value is present. The trend value following the excluded trend value is considered as lasting from the excluded trend value.

The episode analysis displayed in FIG. 31 allows medical personal to quickly and efficiently evaluate trends in a patients ECG allowing a quicker response to deviations that may be of concern.

Recovery Analysis

Recovery is defined as the declining of a parameter from a previous higher value, measured in percent of the maximum trend value preceding the current time. Recovery analysis evaluates the declining of a parameter after a high value as well as the existence of a reperfusion peak. Recovery analysis can be performed on more than one segment to determine time to percent recovery for each segment. Each segment can then be analyzed regardless of the other segments. The recovery at predefined time(s) is calculated based on all data collected before the specified time.

The following parameters can be set before recovery analysis is performed. The time at which thrombolytic therapy will start is set. If the start time of therapy is not set, the start time of therapy is considered to be the same as the start time of monitoring. The time period to search recovery shares is set, and will be the same as the time period for the present segment. The minimum time under limit to accept recovery is set along with the maximum time gap to interpolate. It should be noted that the time period of where to look for recovery shares must not exceed the end of the segment being analyzed. Trend parameters based on corrupted averaged complexes are excluded from the analysis. The excluded times are treated as non-existing (a gap in the trend) during analysis.

The monitored time 318 and the analyzed time 320, displayed during recovery analysis are the same as described above with respect to the episode analysis. During recovery analysis, maximum or extreme value 342 is a dynamic value changing over time, reflecting the maximum trend value monitored up to that point in time.

Looking for shares of recovery, the first time the defined conditions are fulfilled is selected as the time to that percent recovery. Although it could occur that you later get a higher maximum value at a second time the condition is fulfilled, this second occurrence need not be identified. On the other hand, if the user wishes to identify the second occurrence, the user could define a new segment with recovery analysis.

When looking for recovery share at a specific point in time, the maximum value for the trend monitored to that point in time should be used when calculating recovery share. For two different points in time, you could get two different maximum values to base recovery calculations on, and different segments could be used for each.

Time to percentage recovery can be determined using recovery analysis. Time to percentage recovery is the time at which the trend curve declines below a predetermined percentage of the maximum value (percent share limit) for the trend monitored. Linear interpolation between consecutive trend values can be used to define the recovery share, unless a gap between consecutive trend values is larger than the maximum gap to interpolate. The actual time for percentage recovery is the time when the interpolated line crosses the percent share limit provided that the following "minimum time under limit to accept recovery" period of trend data is below the percent share limit. If the following period of trend data is above the limit, analysis continues until the time to the percentage recovery is determined.

If interpolation is not performed, the time for percentage recovery is determined as the time the first trend value falls below the percent share limit provided that there is no value within the time "minimum time under limit to accept recovery" exceeding the percent share limit. This time period is measured from the time of percent recovery. If the conditions for percentage recovery are not met, the time for percentage recovery is left undefined. Preferably, time to percentage recovery is measured from the start of thrombolysis.

Recovery share at predefined point(s) of time can also be analyzed. Recovery share at predefined time(s), is the recovery share relative the maximum value at the set or predefined time(s). Linear interpolation between consecutive trend values can be used to define the recovery share unless a gap between consecutive trend values is larger than the maximum gap to interpolate. The recovery share at a predefined time is the value closest to that predefined time but not further than 10 minutes away. If two values are of equal distance to the predefined time, the earliest value of the two is selected. If no value is defined (not even an interpolated line if interpolation is used) within a 20 minute window, recovery at the predefined time is left undefined. Preferably, the time at which each recovery share is measured is determined from the start of thrombolysis. If the time for maximum value equals the predefined time, the recovery share at the predefined time is zero. Since time to percentage recovery requires that the signal be below the limit a certain period of time and recovery at the predefined time does not, conflicting results may occur.

Recovery analysis can be customized by changing variables that are used in the algorithms for recovery analysis.

The user may set up two different times at which to measure recovery, both defined from the start of thrombolysis. The user may also set up to four different levels of recovery for which time from start of thrombolysis is measured. If left unset, the variables for performing recovery analysis are assigned default values. For example, the minimum time under limit to accept recovery is assigned a 10 minute default value (from time of recovery). The maximum gap to interpolate is set to 600 seconds, although if less than the average period, no interpolation will be performed. The first time at which recovery share is measured is set to 60 minutes. The second time at which recovery share is measured is set to 90 minutes. The first measured time to recovery share is to 20% recovery. The second measured time to recovery share is to 30% recovery.

The third measured time to recovery share is to 50% recovery. The fourth measured time to recovery share is to 70% recovery.

Figure 32:
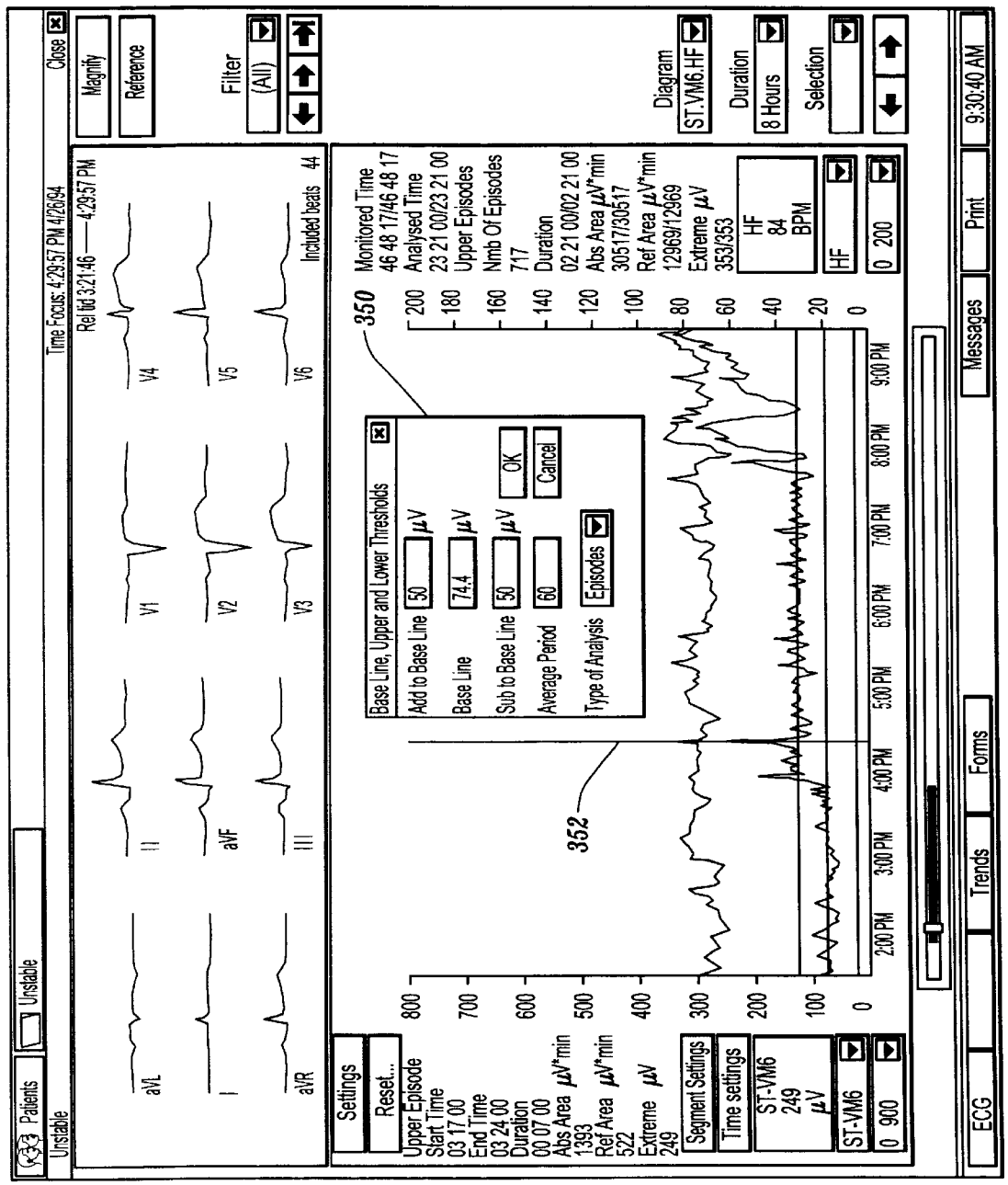
FIG. 32 illustrates another example of a display showing analyzed results.

For both episode and recovery analysis, the displayed trends may be controlled and manipulated to achieve the most useful and efficient results. For example, displayed trends may be divided into segments. As shown in FIG. 32, a dialog box 350 allows a user to provide segment specific settings. The dialog box includes the segment properties and from the dialog box, it is possible to change any of the settings for the segment marked as beginning at cursor 352. More specifically, the type of analysis (episode or recovery), along with the averaging period are selected for the segment. Baseline can be entered if episode analysis is selected, in the unit given on the axis in the trend graph. Upper and lower thresholds can be set if episode analysis is selected. The thresholds represent a distance from the baseline and are in the same units as the baseline.

When analysis is started for a specific parameter, the entire recording is regarded as one segment. It is then possible to divide the recording into up to ten segments, with each segment having its own individual start/stop times, averaging time, type of analysis, baseline parameter, and upper/lower threshold parameters. The start time for the segment created at start-up is the average time before the time of the first trend value. The end time for the segment created at start-up is the time of the last trend value. The baseline is set to the value of the first trend value in the segment and then refined later. The other parameters are set according to the default settings.

Each segment can be divided into two segments. The cursor 352 is positioned to mark where the first segment ends and the second segment starts. After dividing the segment, both segments will have the same averaged time, type of analysis, baseline and threshold, as the original segment. The settings for each segment can then be changed or modified as desired. The start time of the first segment is the start time of the original segment. The end time of the second segment is the end time of the original segment. The end time of the first segment and the start time of the second segment is the time marked by the cursor.

Two segments may also be merged into one. Upon merging, the resulting segment has the averaged time, type of analysis, baseline and thresholds as the first of the two segments. The start time is the start time of the first segment and the end time is the end time of the second segment.

A trend value belongs to a segment if the time of the trend value is after the start of the segment of the segment and prior to or at the same time as the end of the segment.

Computer executable software code for performing processing of the trend parameters and/or analysis of the trend curves in the above-described episode and/or recovery analysis can be provided on a computer readable storage medium such as a CD ROM, floppy disk, etc. The software can be executed and/or entered into workstation 11, for example, by an end user of the monitoring system.

Figure 16:
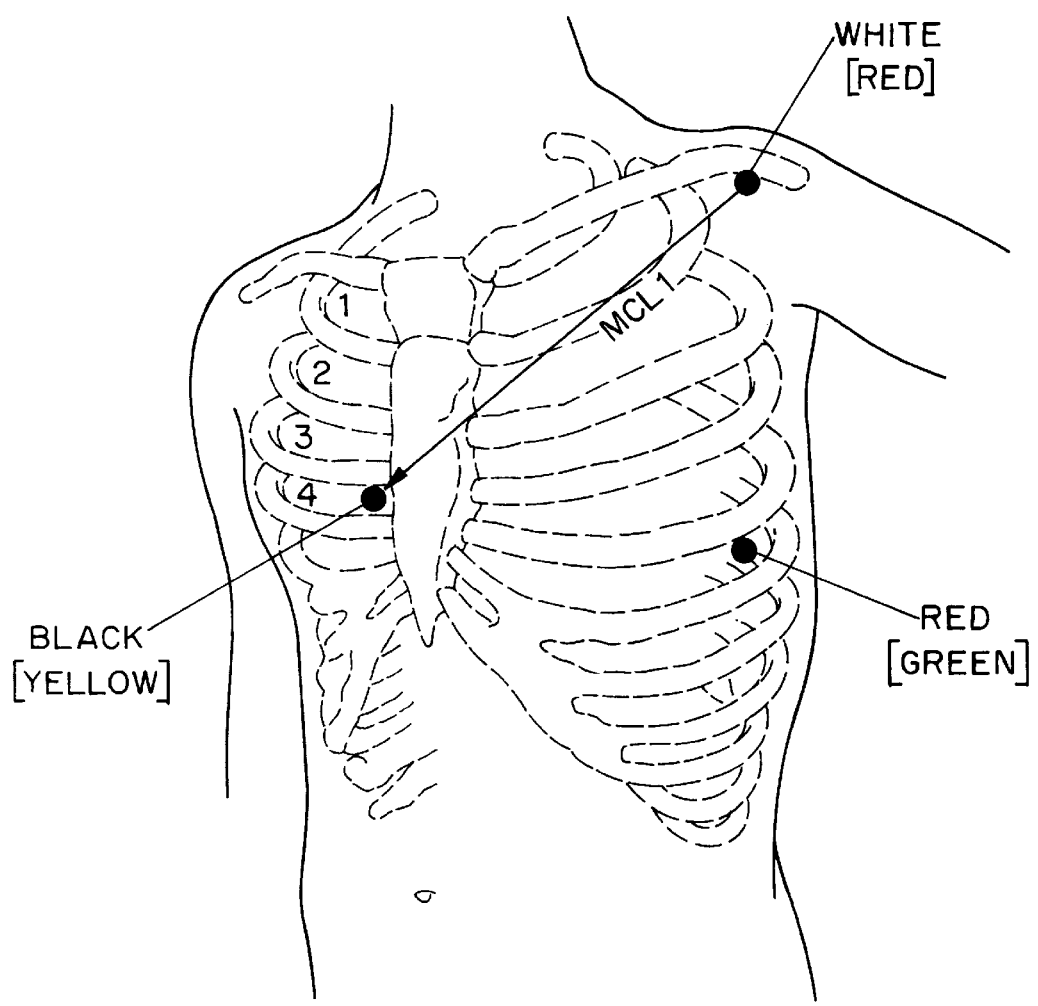
FIG. 16 shows the placement of a 3-lead electrode leadset on a patient's torso.
Figure 17:
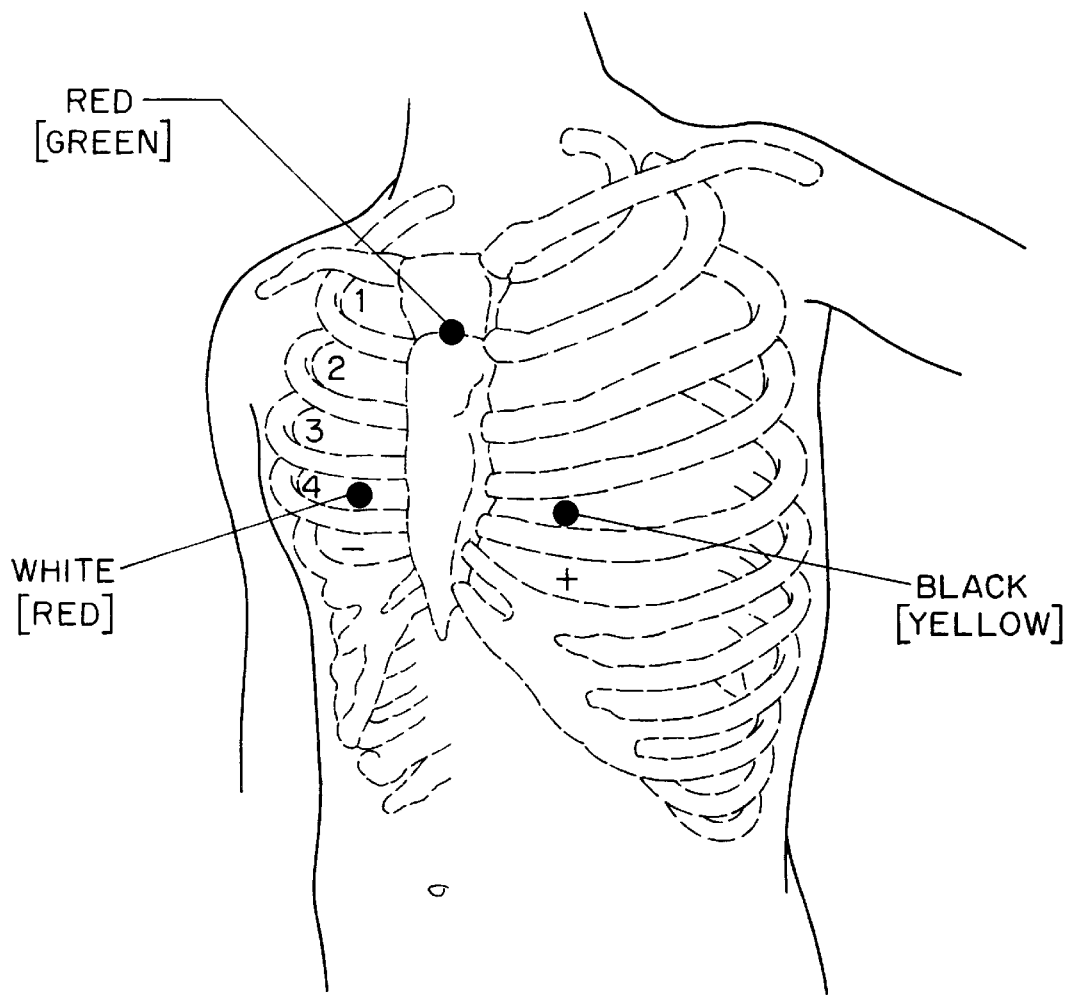
FIG. 17 shows the placement of a 3-lead electrode leadset on a patient's torso for paced patients.
Figure 18:
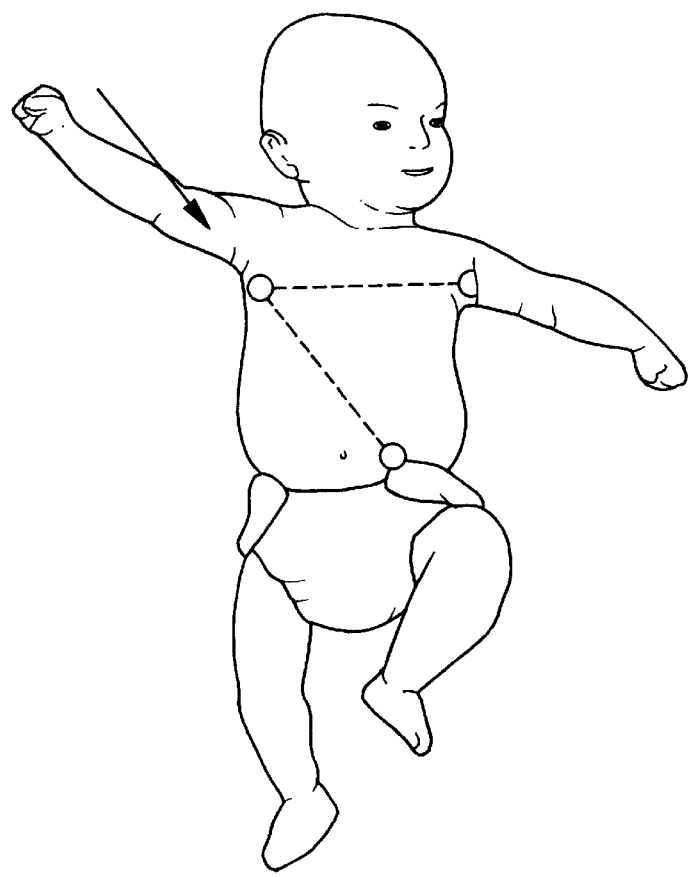
FIG. 18 shows the placement of a 3-lead electrode leadset on an infant.
Figure 19:
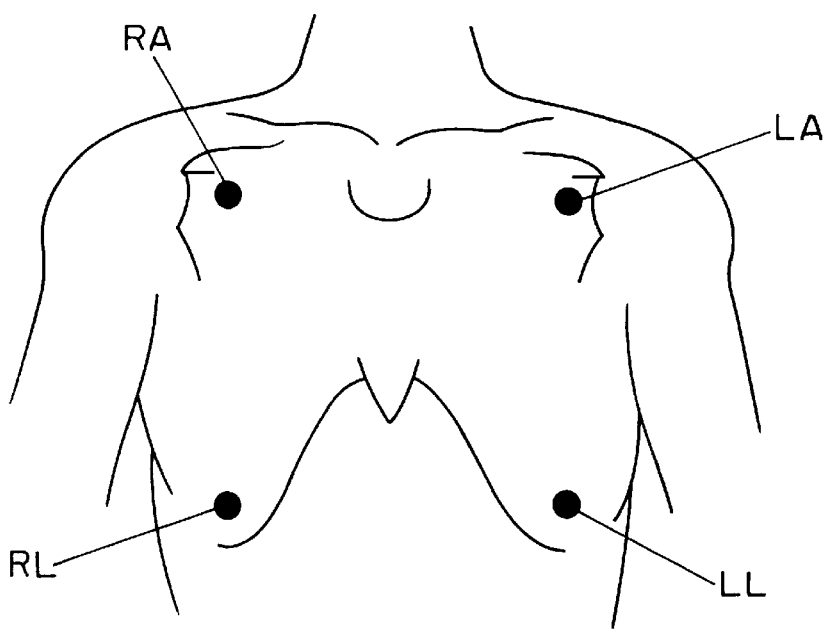
FIG. 19 shows the placement of a 4-lead electrode leadset on a patient's torso.
Figure 20:
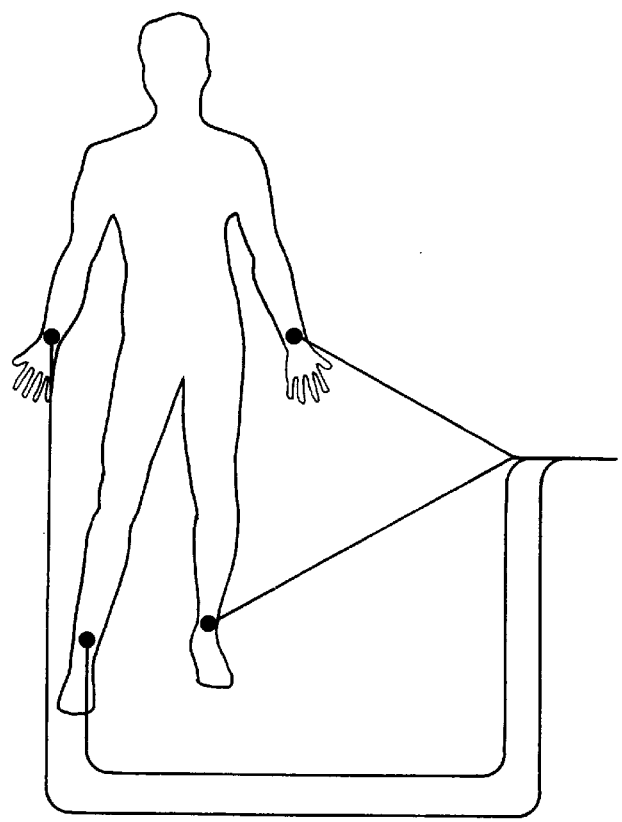
FIG. 20 shows the placement of a 4-lead electrode leadset on a patient's limbs.
Figure 22:
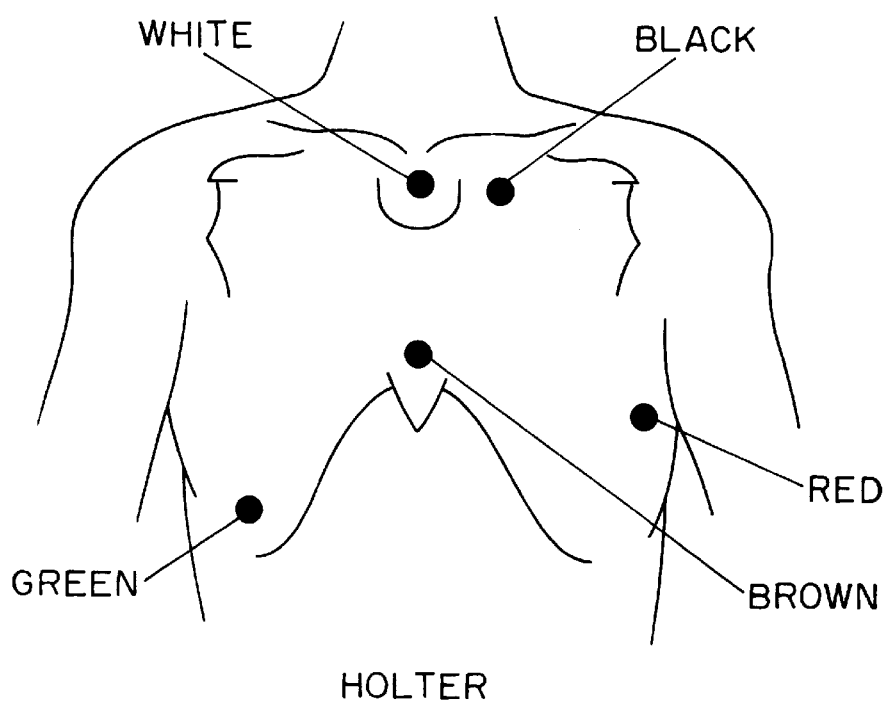
FIG. 22 shows the placement of a 5-lead electrode leadset on a patient's torso for holter recording.
Figure 21:
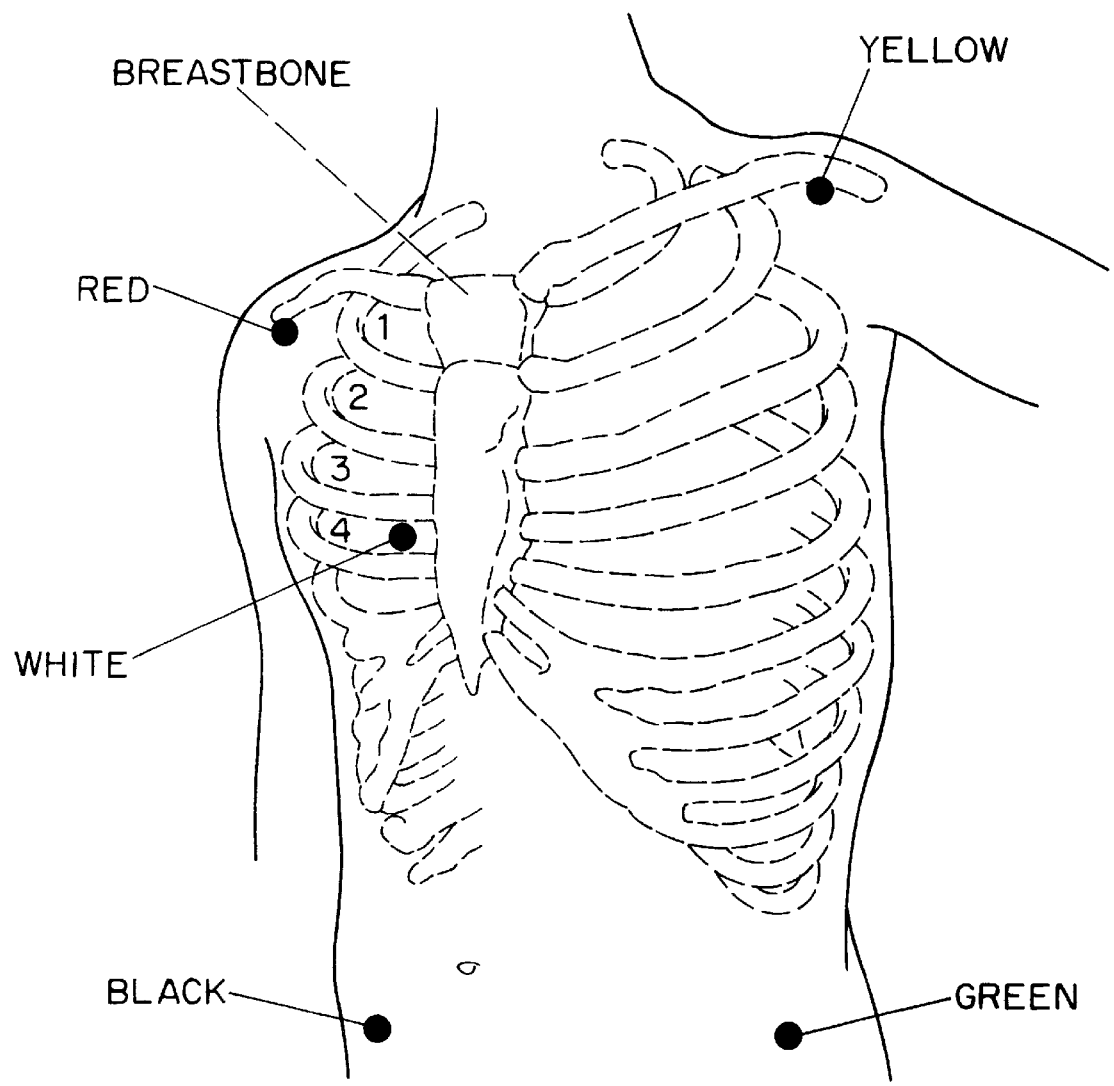
FIG. 21 shows the placement of a 5-lead electrode leadset on a patient's torso for monitoring.
Figure 23:
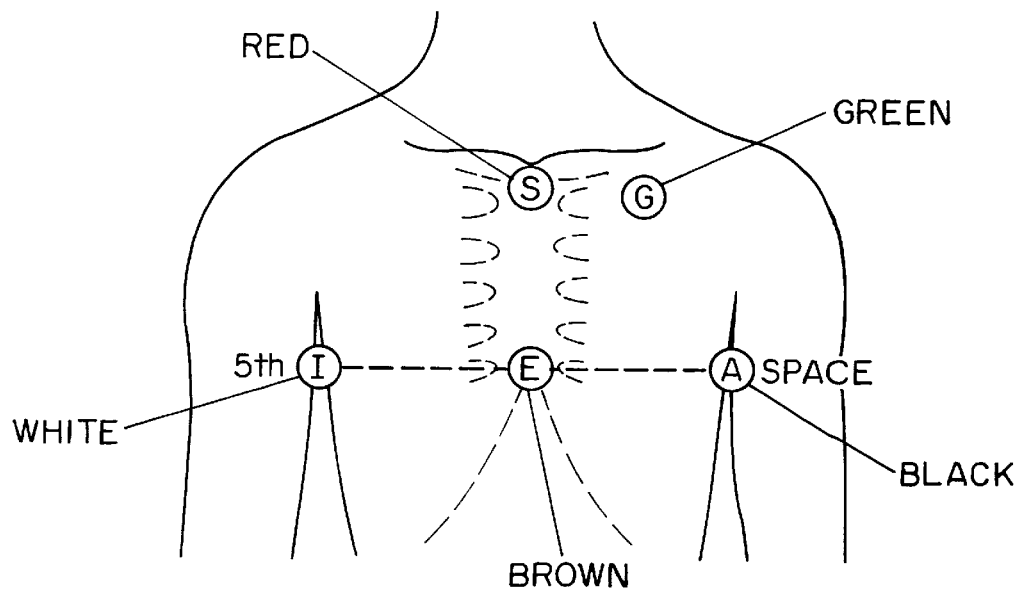
FIG. 23 shows the placement of a 5-lead electrode leadset on a patient according to the EASI leadset.
Figure 24:
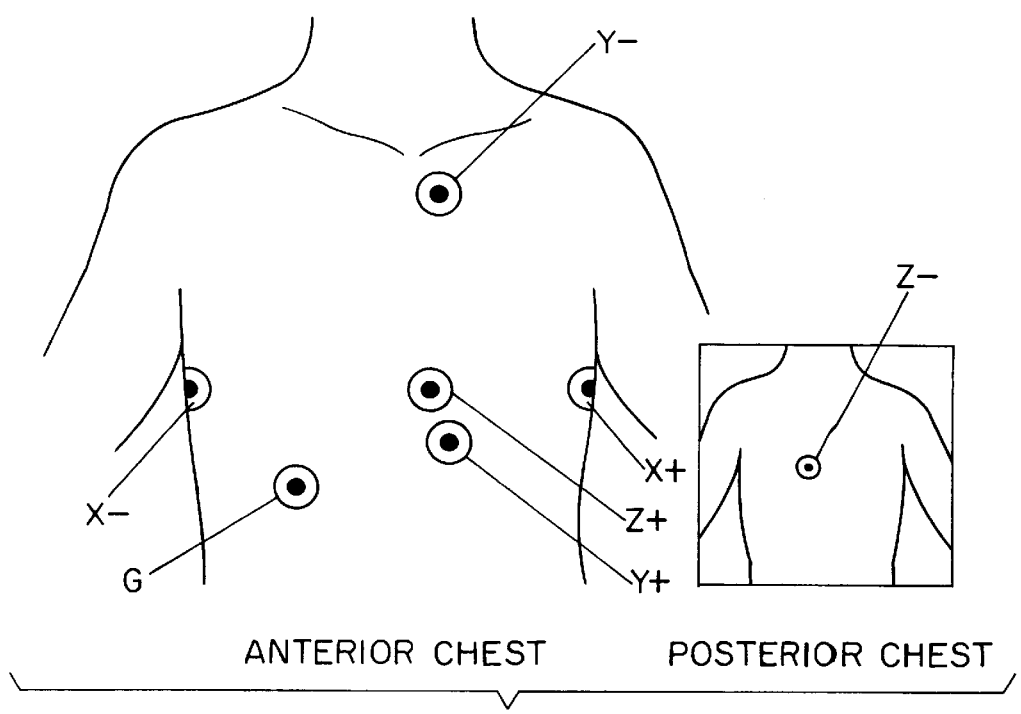
FIG. 24 shows the placement of a 7-lead electrode leadset on a patient's torso for late potential analysis.
Figure 25:
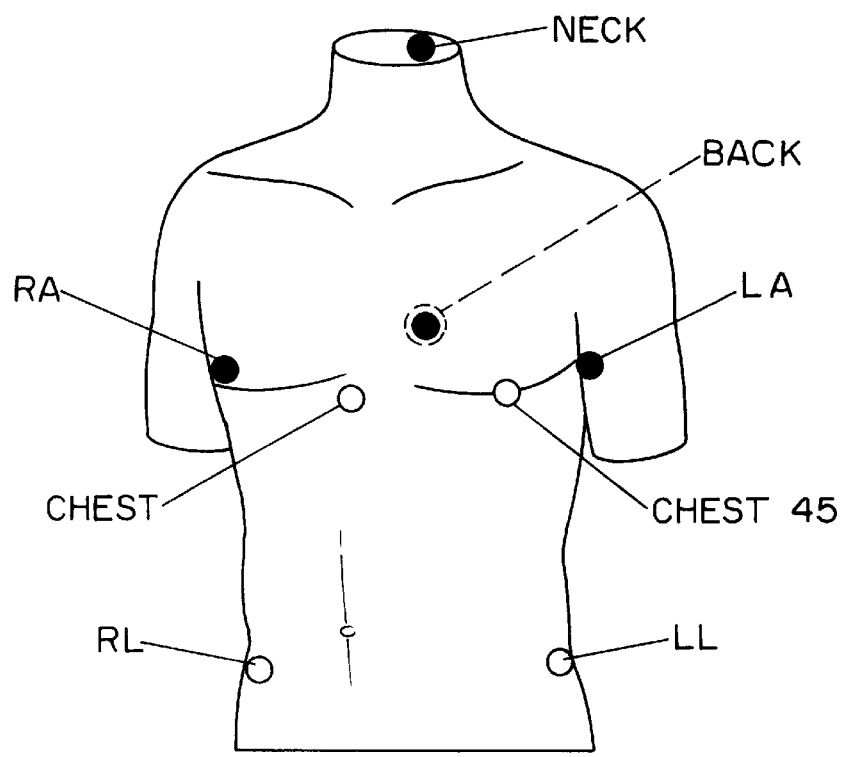
FIG. 25 shows the placement of an 8-lead electrode leadset on a patient's torso according to Frank.
Figure 26:
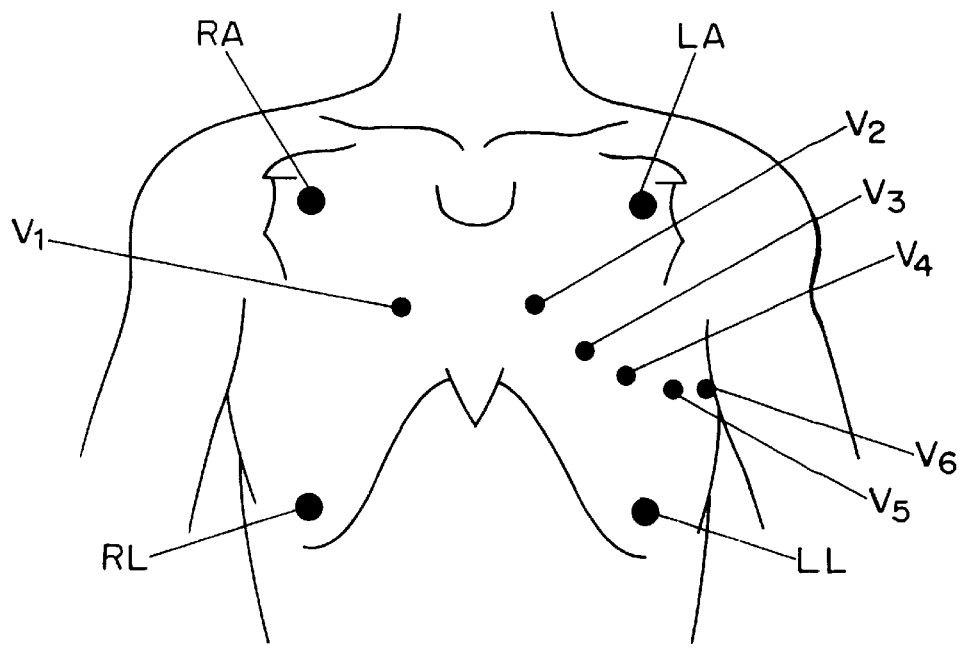
FIG. 26 shows the placement of a 10-lead electrode leadset on a patient's torso to get true 12-lead ECG (RA and LA may be placed on arms, RL and LL further down on legs).

The invention is not limited to the systems and methods illustrated in the drawings and described above. Modifications and variations are possible within the inventive concept. For example, in addition to the electrode leadsets discussed above, the following leadsets may be used: the 3-lead electrode leadsets of FIGS. 16, 17, and 18, the 4-lead electrode leadsets of FIGS. 19 and 20, the 5-lead electrode leadsets of FIGS. 21, 22, and 23 (the EASI leadset and algorithm of FIG. 23 are covered by U.S. Pat. No. 4,850,370, issued Jul. 25, 1989), the 7-lead electrode leadset of FIG. 24, the 8-lead electrode leadset of FIG. 25 according to Frank, and the 10-lead electrode leadset of FIG. 26. In addition, body surface mapping (normally with 48 electrodes) may be applied to the invention. Accordingly, the disclosure should not be construed as limiting the scope of the following claims, which specifically define the invention.

What is claimed is:

1. A myocardial analysis and monitoring method, comprising the steps of:

receiving a number of ECG signals relating to a heartbeat of at least one patient;

converting the received number of ECG signals into three perpendicular ECG signals;

determining an average heartbeat from the ECG signals;

calculating a plurality of parameters related to a condition of each patient from said number of ECG signals;

storing information representative of a value of said plurality of parameters related to the condition of each patient in storage;

repeating the steps of determining said average heartbeat, calculating said plurality of parameters and storing said information for as long as ECG signals continue to be received or until the storage is full;

displaying at least a portion of the stored information as a graphical display, the graphical display representing a trend of at least one of the plurality of parameters;

analyzing the displayed trend of the at least one of the plurality of parameters;

displaying at least one result of the analysis, wherein said analyzing step comprises detecting episodes, each episode comprising a predetermined number of trend values above a predetermined upper threshold level or below a predetermined lower threshold level occurring within a predetermined period of time of each other.

2. A myocardial analysis and monitoring method as recited in claim 1, further comprising a step of displaying the number of detected episodes.

3. A myocardial analysis and monitoring method as recited in claim 1, wherein said analyzing step comprises detecting an amount of time for a parameter to decline from a maximum value to a predefined value.

4. A myocardial analysis and monitoring method as recited in claim 3, further comprising a step of displaying the detected amount of time.

5. A myocardial analysis and monitoring method as recited in claim 3, wherein the detected amount of time begins at a start of a patient therapy.

6. A myocardial analysis and monitoring method as recited in claim 5, wherein the patient therapy comprises thrombolysis.

7. A myocardial analysis and monitoring method as recited in claim 1, wherein said analyzing step comprises detecting an amount of recovery of a parameter at a predetermined time.

8. A myocardial analysis and monitoring method as recited in claim 7, further comprising a step of displaying the detected amount of recovery.

9. A myocardial analysis and monitoring apparatus, comprising:

at least one input receiving a number of ECG signals relating to a heartbeat of at least one patient;

a processor for converting the received number of ECG signals into three perpendicular ECG signals, determining an average heartbeat from the ECG signals, calculating a plurality of parameters related to a condition of each patient from said number of ECG signals and storing information representative of a value of said plurality of parameters related to the condition of each patient in storage, wherein determining of said average heartbeat, calculating of said plurality of parameters and storing of said information continues for as long as ECG signals continue to be received or until the storage is full;

a display for displaying at least a portion of the stored information as a graphical display, the graphical display representing a trend of at least one of the plurality of parameters; and an analyzer for analyzing the displayed trend of the at least one of the plurality of parameters, the display displaying at least one result of the analysis, wherein said analyzer detects episodes, each episode comprising a predetermined number of trend values above a predetermined upper threshold level or below a predetermined lower threshold level occurring within a predetermined period of time of each other.

10. A myocardial analysis and monitoring apparatus as recited in claim 9, wherein the display displays the number of detected episodes.

11. A myocardial analysis and monitoring apparatus as recited in claim 9, wherein said analyzer detects an amount of time for a parameter to decline from a maximum value to a predefined value.

12. A myocardial analysis and monitoring apparatus as recited in claim 11, wherein the display displays the detected amount of time.

13. A myocardial analysis and monitoring apparatus as recited in claim 11, wherein the detected amount of time begins at a start of a patient therapy.

14. A myocardial analysis and monitoring apparatus as recited in claim 13, wherein the patient therapy comprises thrombolysis.

15. A myocardial analysis and monitoring apparatus as recited in claim 9, wherein said analyzer detects an amount of recovery of a parameter at a predetermined time.

16. A myocardial analysis and monitoring method as recited in claim 15, wherein the display displays the detected amount of recovery.

17. A computer executable software code stored on a computer readable medium, the code for performing myocardial analysis and monitoring, the code comprising:

code for controlling a monitoring system for receiving a number of ECG signals relating to a heartbeat of at least one patient;

code for converting the received number of ECG signals into three perpendicular ECG signals;

code for determining an average heartbeat from the ECG signals;

code for calculating a plurality of parameters related to a condition of each patient from said number of ECG signals;

code for storing information representative of a value of said plurality of parameters related to the condition of each patient in storage, the determination of said average heartbeat, calculation of said plurality of parameters and storing of said information being performed for as long as ECG signals continue to be received or until the storage is full;

code for displaying at least a portion of the stored information as a graphical display, the graphical display representing a trend of at least one of the plurality of parameters;

code for analyzing the displayed trend of the at least one of the plurality of parameters;

code for displaying at least one result of the analysis, wherein said code for analyzing comprises code for detecting episodes, each episode comprising a predetermined number of trend values above a predetermined upper threshold level or below a predetermined lower threshold level occurring within a predetermined period of time of each other.

18. A computer executable software code as recited in claim 17, wherein said code for analyzing comprises code for detecting an amount of time for a parameter to decline from a maximum value to a predefined value.

19. A computer executable software code as recited in claim 17, wherein said code for analyzing comprises code for detecting an amount of recovery of a parameter at a predetermined time.

20. A myocardial analysis and monitoring method, comprising the steps of:

receiving a number of ECG signals relating to a heartbeat of at least one patient;

converting the received number of ECG signals into three perpendicular ECG signals;

determining, for each occasion that a number of ECG signals is received, whether or not the three perpendicular ECG signals correspond to a beat to be included in an average heartbeat;

determining an average heartbeat from only those three perpendicular ECG signals determined to correspond to a beat to be included in the average heartbeat:

calculating a plurality of parameters related to a condition of each patient from said three perpendicular ECG signals;

storing information representative of a value of said plurality of parameters related to the condition of each patient in storage;

repeating the steps of determining said average heartbeat, calculating said plurality of parameters and storing said information for as long as ECG signals continue to be received or until the storage is full;

displaying at least a portion of the stored information as a graphical display, the graphical display representing a trend of at least one of the plurality of parameters;

analyzing the displayed trend of the at least one of the plurality of parameters;

displaying at least one result of the analysis.

21. A myocardial analysis and monitoring method as recited in claim 20, wherein said analyzing step comprises detecting episodes, each episode comprising a predetermined number of trend values above a predetermined upper threshold level or below a predetermined lower threshold level occurring within a predetermined period of time of each other.

22. A myocardial analysis and monitoring method as recited in claim 21, further comprising a step of displaying the number of detected episodes.

23. A myocardial analysis and monitoring method as recited in claim 20, wherein said analyzing step comprises detecting an amount of time for a parameter to decline from a maximum value to a predefined value.

24. A myocardial analysis and monitoring method as recited in claim 23, further comprising a step of displaying the detected amount of time.

25. A myocardial analysis and monitoring method as recited in claim 23, wherein the detected amount of time begins at a start of a patient therapy.

26. A myocardial analysis and monitoring method as recited in claim 25, wherein the patient therapy comprises thrombolysis.

27. A myocardial analysis and monitoring method as recited in claim 20, wherein said analyzing step comprises detecting an amount of recovery of a parameter at a predetermined time.

28. A myocardial analysis and monitoring method as recited in claim 27, further comprising a step of displaying the detected amount of recovery.

29. A myocardial analysis and monitoring apparatus, comprising:
at least one input receiving a number of ECG signals relating to a heartbeat of at least one patient;
a processor for converting the received number of ECG signals into three perpendicular ECG signals, determining an average heartbeat from the three perpendicular ECG signals, calculating a plurality of parameters related to a condition of each patient from said three perpendicular ECG signals and storing information representative of a value of said plurality of parameters related to the condition of each patient in storage, wherein determining of said average heartbeat, calculating of said plurality of parameters and storing of said information continues for as long as ECG signals continue to be received or until the storage is full;
a display for displaying at least a portion of the stored information as a graphical display, the graphical display representing a trend of at least one of the plurality of parameters; and
an analyzer for analyzing the displayed trend of the at least one of the plurality of parameters, the display displaying at least one result of the analysis.

30. A myocardial analysis and monitoring apparatus as recited in claim 29, wherein said analyzer detects episodes, each episode comprising a predetermined number of trend values above a predetermined upper threshold level or below a predetermined lower threshold level occurring within a predetermined period of time of each other.

31. A myocardial analysis and monitoring apparatus as recited in claim 30, wherein the display displays the number of detected episodes.

32. A myocardial analysis and monitoring apparatus as recited in claim 29, wherein said analyzer detects an amount of time for a parameter to decline from a maximum value to a predefined value.

33. A myocardial analysis and monitoring apparatus as recited in claim 32, wherein the display displays the detected amount of time.

34. A myocardial analysis and monitoring apparatus as recited in claim 32, wherein the detected amount of time begins at a start of a patient therapy.

35. A myocardial analysis and monitoring apparatus as recited in claim 34, wherein the patient therapy comprises thrombolysis.

36. A myocardial analysis and monitoring apparatus as recited in claim 29, wherein said analyzer detects an amount of recovery of a parameter at a predetermined time.

37. A myocardial analysis and monitoring method as recited in claim 36, wherein the display displays the detected amount of recovery.

38. A computer executable software code stored on a computer readable medium, the code for performing myocardial analysis and monitoring, the code comprising:
code for controlling a monitoring system for receiving a number of ECG signals relating to a heartbeat of at least one patient;
code for converting the received number of ECG signals into three perpendicular ECG signals;
code for determining an average heartbeat from the three perpendicular ECG signals;
code for calculating a plurality of parameters related to a condition of each patient from said three perpendicular ECG signals;
code for storing information representative of a value of said plurality of parameters related to the condition of each patient in storage, the determination of said average heartbeat, calculation of said plurality of parameters and storing of said information being performed for as long as ECG signals continue to be received or until the storage is full;
code for displaying at least a portion of the stored information as a graphical display, the graphical display representing a trend of at least one of the plurality of parameters;
code for analyzing the displayed trend of the at least one of the plurality of parameters;
code for displaying at least one result of the analysis.

39. A computer executable software code as recited in claim 38, wherein said code for analyzing comprises code for detecting episodes, each episode comprising a predetermined number of trend values above a predetermined upper threshold level or below a predetermined lower threshold level occurring within a predetermined period of time of each other.

40. A computer executable software code as recited in claim 38, wherein said code for analyzing comprises code for detecting an amount of time for a parameter to decline from a maximum value to a predefined value.

41. A computer executable software code as recited in claim 38, wherein said code for analyzing comprises code for detecting an amount of recovery of a parameter at a predetermined time.

42. A myocardial analysis and monitoring method, comprising the steps of:
receiving a number of ECG signals relating to a heartbeat of at least one patient;
converting the received number of ECG signals into three perpendicular ECG signals;
determining an average heartbeat from the three perpendicular ECG signals;
calculating a plurality of parameters related to a condition of each patient from said three perpendicular ECG signals;
storing information representative of a value of said plurality of parameters related to the condition of each patient in storage;
repeating the steps of determining said average heartbeat, calculating said plurality of parameters and storing said information for as long as ECG signals continue to be received or until the storage is full;
displaying at least a portion of the stored information as a graphical display, the graphical display representing a trend of at least one of the plurality of parameters;
analyzing the displayed trend of the at least one of the plurality of parameters;
displaying at least one result of the analysis,
wherein said analyzing step comprises detecting episodes, each episode comprising a predetermined number of trend values above a predetermined upper threshold level or below a predetermined lower threshold level occurring within a predetermined period of time of each other.

43. A myocardial analysis and monitoring apparatus, comprising:

at least one input receiving a number of ECG signals relating to a heartbeat of at least one patient;

a processor for converting the received number of ECG signals into three perpendicular ECG signals, determining an average heartbeat from the three perpendicular ECG signals, calculating a plurality of parameters related to a condition of each patient from said three perpendicular ECG signals and storing information representative of a value of said plurality of parameters related to the condition of each patient in storage, wherein determining of said average heartbeat, calculating of said plurality of parameters and storing of said information continues for as long as ECG signals continue to be received or until the storage is full;

a display for displaying at least a portion of the stored information as a graphical display, the graphical display representing a trend of at least one of the plurality of parameters; and an analyzer for analyzing the displayed trend of the at least one of the plurality of parameters, the display displaying at least one result of the analysis, wherein said analyzer detects episodes, each episode comprising a predetermined number of trend values above a predetermined upper threshold level or below a predetermined lower threshold level occurring within a predetermined period of time of each other.

44. A computer executable software code stored on a computer readable medium, the code for performing myocardial analysis and monitoring, the code comprising:

code for controlling a monitoring system for receiving a number of ECG signals relating to a heartbeat of at least one patient;

code for converting the received number of ECG signals into three perpendicular ECG signals;

code for determining an average heartbeat from the three perpendicular ECG signals;

code for calculating a plurality of parameters related to a condition of each patient from said three perpendicular ECG signals;

code for storing information representative of a value of said plurality of parameters related to the condition of each patient in storage, the determination of said average heartbeat, calculation of said plurality of parameters and storing of said information being performed for as long as ECG signals continue to be received or until the storage is full;

code for displaying at least a portion of the stored information as a graphical display, the graphical display representing a trend of at least one of the plurality of parameters;

code for analyzing the displayed trend of the at least one of the plurality of parameters;

code for displaying at least one result of the analysis, wherein said code for analyzing comprises code for detecting episodes, each episode comprising a predetermined number of trend values above a predetermined upper threshold level or below a predetermined lower threshold level occurring within a predetermined period of time of each other.

* * * * *